United States Patent
Comenzo et al.

(10) Patent No.: US 9,593,332 B2
(45) Date of Patent: Mar. 14, 2017

(54) METHODS AND COMPOSITIONS FOR TARGETING IMMUNOGLOBULINS

(71) Applicant: TUFTS MEDICAL CENTER, Boston, MA (US)

(72) Inventors: Raymond Comenzo, Newton, MA (US); Ping Zhou, Brighton, MA (US); Xun Ma, Brighton, MA (US)

(73) Assignee: TUFTS MEDICAL CENTER, Boston, MA (US)

( * ) Notice: Subject to any disclaimer, the term of this patent is extended or adjusted under 35 U.S.C. 154(b) by 0 days.

(21) Appl. No.: 14/760,132

(22) PCT Filed: Jan. 15, 2014

(86) PCT No.: PCT/US2014/011617
§ 371 (c)(1),
(2) Date: Jul. 9, 2015

(87) PCT Pub. No.: WO2014/113431
PCT Pub. Date: Jul. 24, 2014

(65) Prior Publication Data
US 2015/0361429 A1 Dec. 17, 2015

Related U.S. Application Data

(60) Provisional application No. 61/752,721, filed on Jan. 15, 2013.

(51) Int. Cl.
*C12N 15/11* (2006.01)
*C12N 15/113* (2010.01)
*C07K 16/00* (2006.01)

(52) U.S. Cl.
CPC ............ *C12N 15/113* (2013.01); *C07K 16/00* (2013.01); *C07K 2317/515* (2013.01); *C12N 2310/14* (2013.01)

(58) Field of Classification Search
CPC .......................... C12N 15/113; C12N 2310/11
See application file for complete search history.

(56) References Cited

U.S. PATENT DOCUMENTS

| 5,814,318 | A | 9/1998 | Lonberg et al. | |
|---|---|---|---|---|
| 2004/0002068 | A1 | 1/2004 | Gaiger et al. | |
| 2007/0039072 | A1* | 2/2007 | Khvorova ............ | A61K 31/713 800/286 |
| 2007/0238182 | A1 | 10/2007 | Gaiger et al. | |

FOREIGN PATENT DOCUMENTS

| JP | 2004-75626 A | * | 3/2004 |
|---|---|---|---|
| WO | WO9014430 | | 11/1990 |

OTHER PUBLICATIONS

English translation of JP2004-75626A, pp. 1-17 retrieved on Apr. 26, 2016.*
Arendt et al., "Biologic and genetic characterization of the novel amyloidogenic lambda light chain-secreting human cell lines, ALMC-1 and ALMC-2." Blood. Sep. 1, 2008;112(5):1931-41.
Comenzo et al. "Pathobiologic associations of plasma cell (PC) overexpression of Cyclin D1 (CCND1) in systemic AL amyloidosis (AL)" Amyloid. 2010;17(suppl 1):61. abstr OP-044.
Haas et al., "Immunoglobulin heavy chain toxicity in plasma cells is neutralized by fusion to pre-B cells." Proc Natl Acad Sci U S A. Nov. 1984;81(22):7185-8.
Hetz et al., "Fine-tuning of the unfolded protein response: Assembling the IRE1alpha interactome." Mol Cell. Sep. 11, 2009;35(5):551-61.
Hovey et al., "Preclinical development of siRNA therapeutics for AL amyloidosis." Gene Ther. Dec. 2011;18 (12)1150-6.
International Search Report mailed Jul. 8, 2014, Application No. PCT/US2014/011617 filed Jan. 15, 2014. 27 pages.
Jager et al., "The unfolded protein response at the crossroads of cellular life and death during endoplasmic reticulum stress." Biol Cell. May 2012;104(5):259-70.
Katzmann et al., "Serum reference intervals and diagnostic ranges for free kappa and free lambda immunoglobulin light chains: relative sensitivity for detection of monoclonal light chains." Clin Chem. Sep. 2002;48(9):1437-44.
Lefranc et al., "IMGT unique numbering for immunoglobulin and T cell receptor constant domains and Ig superfamily C-like domains." Dev Comp Immunol. 2005;29(3):185-203.
Ohno et al., "The antisense approach in amyloid light chain amyloidosis: identification of monoclonal Ig and inhibition of its production by antisense oligonucleotides in in vitro and in vivo models." J Immunol. Oct. 1, 2002;169(7):4039-45.
Palumbo et al., "Multiple myeloma." N Engl J Med. Mar. 17, 2011;364(11):1046-60.
Phipps et al., "Inhibition of pathologic immunoglobulin-free light chain production by small interfering RNA molecules." Exp Hematol. Nov. 2010;38(11):1006-13.
Zhou et al., "Calreticulin expression in the clonal plasma cells of patients with systemic light-chain (AL-) amyloidosis is associated with response to high-dose melphalan." Blood. Jan. 15, 2008;111(2):549-57.
Zhou et al., "Clonal plasma cell pathophysiology and clinical features of disease are linked to clonal plasma cell expression of cyclin D1 in systemic light-chain amyloidosis." Clin Lymphoma Myeloma Leuk. Feb. 2012;12(1):49-58.
Zhou et al., "CD32B is highly expressed on clonal plasma cells from patients with systemic light-chain amyloidosis and provides a target for monoclonal antibody-based therapy." Blood. Apr. 1, 2008;111(7):3403-6.
Zou et al., "Block in development at the pre-B-II to immature B cell stage in mice without Ig kappa and Ig lambda light chain." J Immunol. Feb. 1, 2003;170(3):1354-61.

* cited by examiner

*Primary Examiner* — Brian Whiteman
(74) *Attorney, Agent, or Firm* — Tanya A. Arenson; Casimir Jones, S.C.

(57) ABSTRACT

The present invention relates to compositions and methods for targeting immunoglobulins and immunoglobulin-producing plasma cells. In particular, the present invention provides nucleic acid based compounds for targeting immunoglobulins for research, screening, and therapeutic applications.

14 Claims, 17 Drawing Sheets

The efficacy of si[*IgLC*] in reducing light chain protein expression by flow cytometry in lambda light chain producing myeloma cell lines and AL patient cells Five CD138-selected lambda patient samples showing reduced intracellular lambda light chains by flow cytometry at 24 hours after transfection with si[IgLC] (arrows)

Fig. 4 (Cont.)
Five CD138-selected lambda patient samples showing reduced intracellular lambda light chains by flow cytometry at 24 hours after transfection with si[IgLC] (arrows)
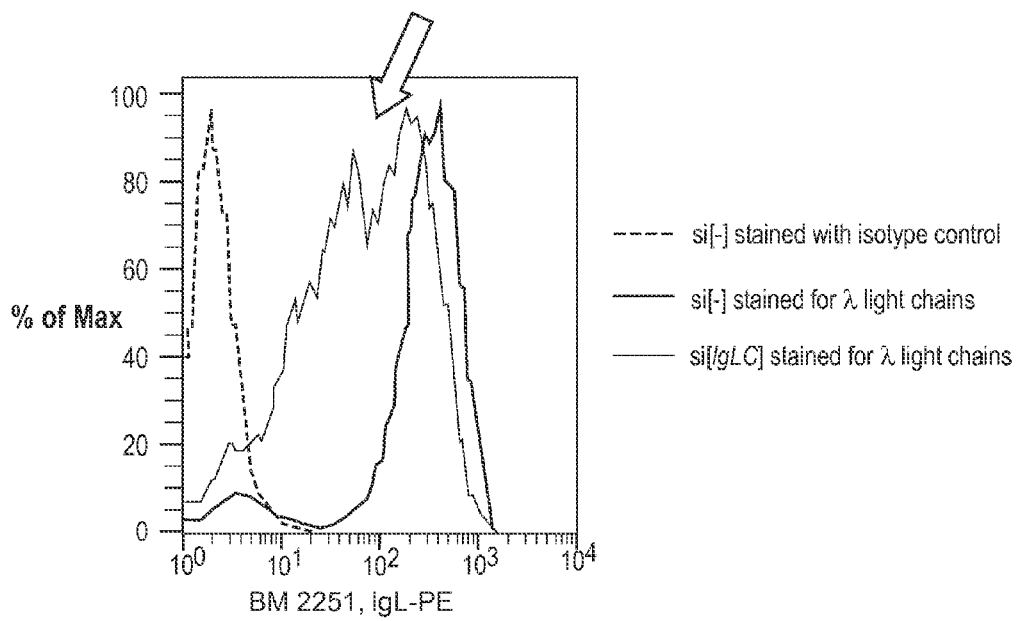
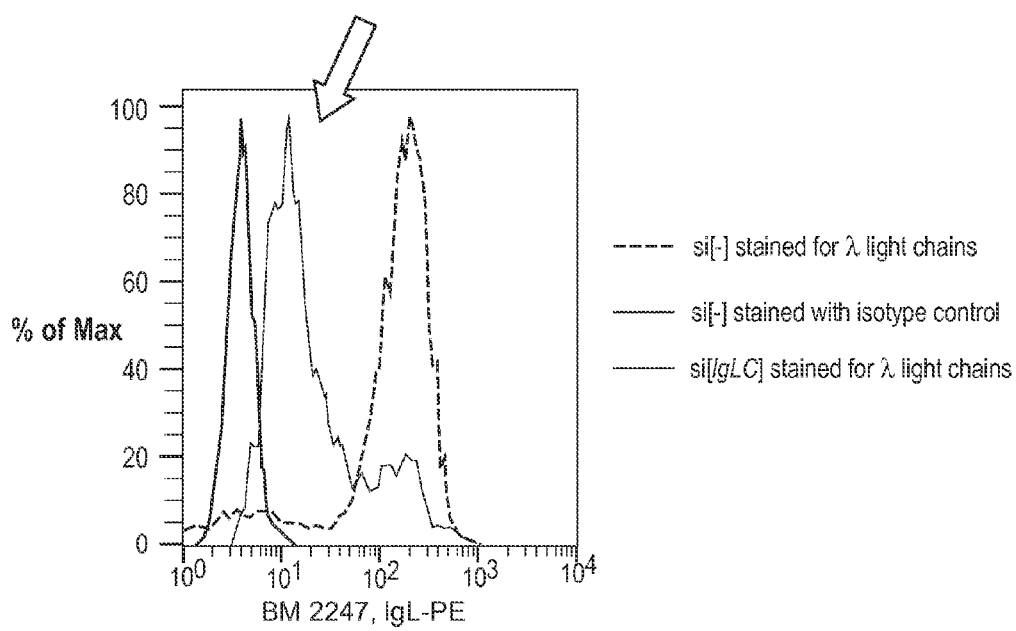

Immunoblot of lambda-restricted patient cells at 24 hours after treatment with si[*IgLC*] showing reduced lambda light chains Reductions in light and heavy chain proteins with siRNA Light chain immunoblots of myeloma cell lines after si[*IgLC*]

Fig. 8
Light chain reduction by flow cytometry and immunblot in H929 myeloma cells after si[*IgKC*]
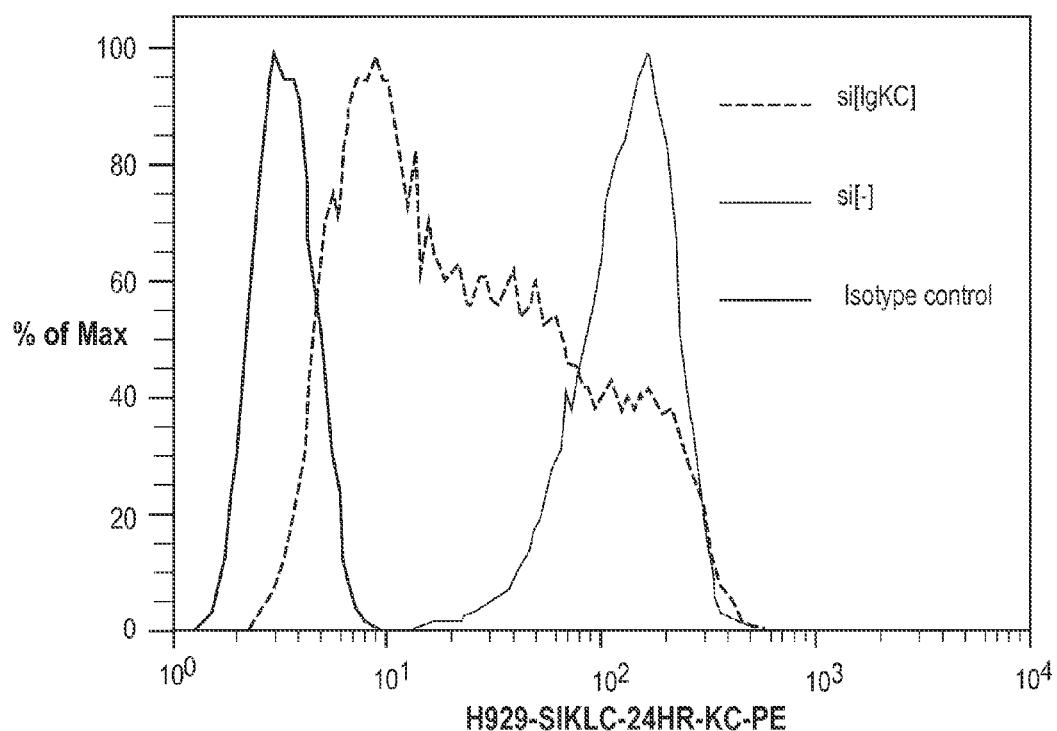
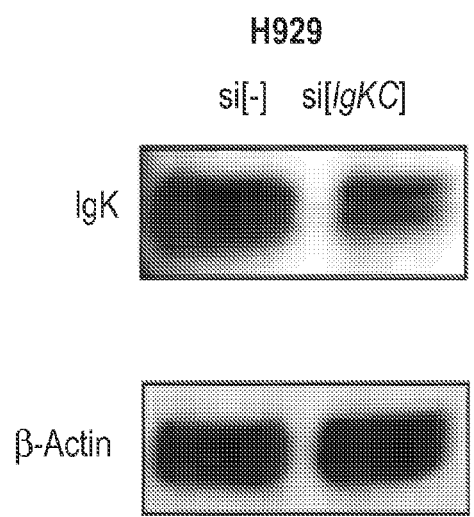

Fig. 9
Flow cytometry with staining for Kappa and Lambda showing effect of combined si[*IgLC+IgKC*] knockdown in a pool of MM1S and H929 cells at a 1:1 ratio
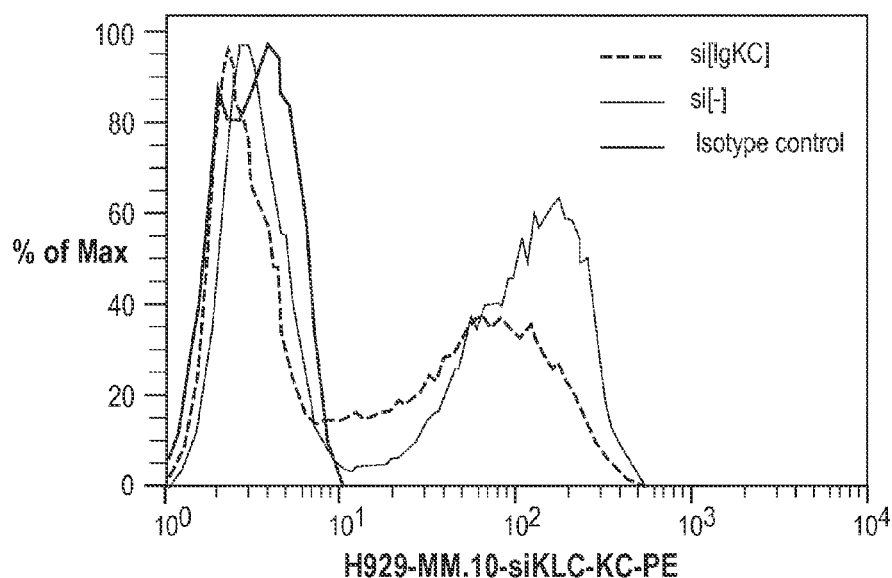
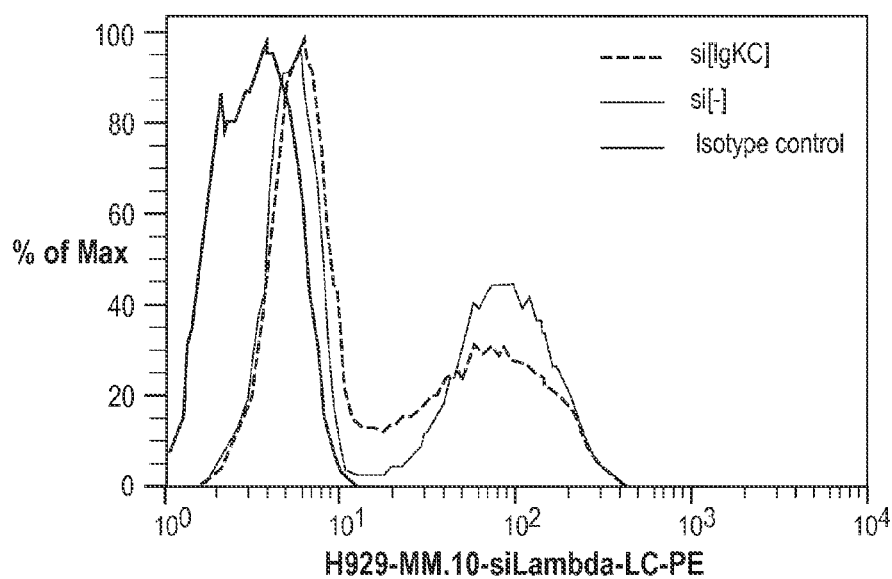

Fig. 10
Knockdown of lambda light chains leaves unmated heavy chains that associate with GRP78
A.
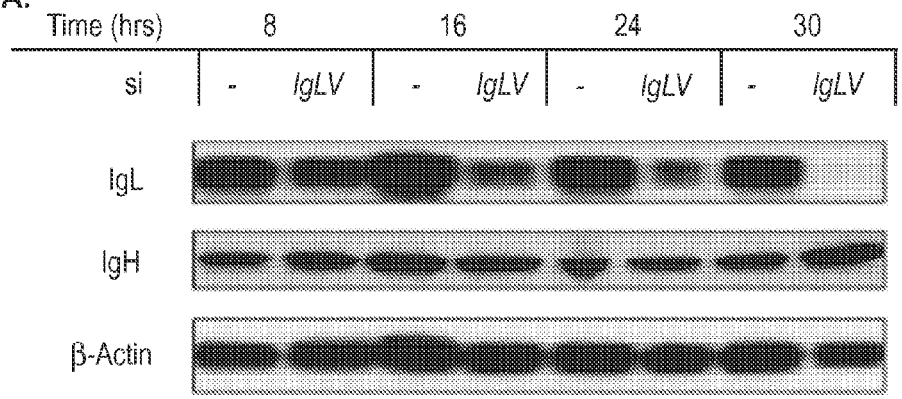
B.
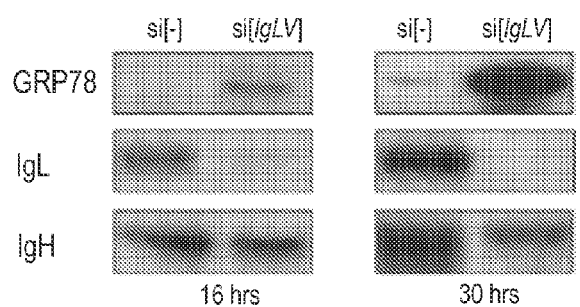
C.
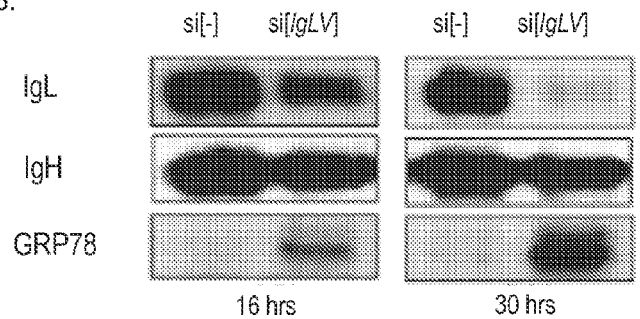

Immunoblots of patient specimen #2251 showing reduction of lambda light chains and increase in GRP78 at 24 hours after si[*IgLC*] transfection

Fig. 12
The rapid onset of the unfolded protein response after lambda light chain knockdown
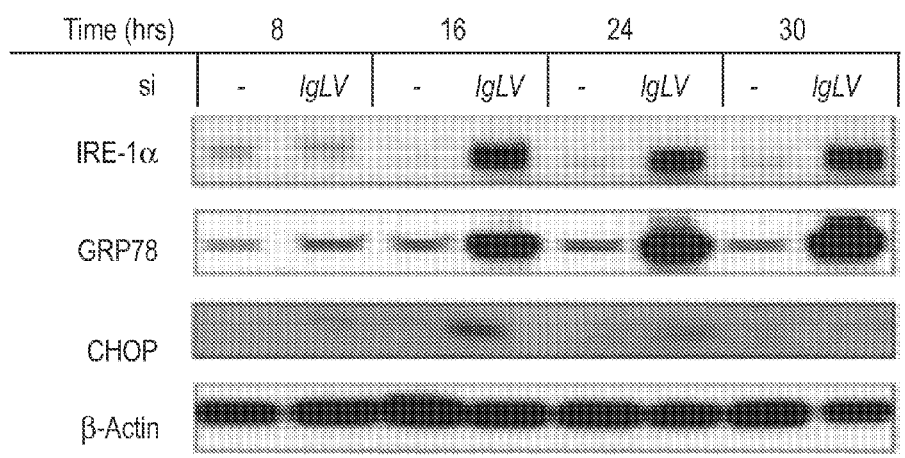
A.
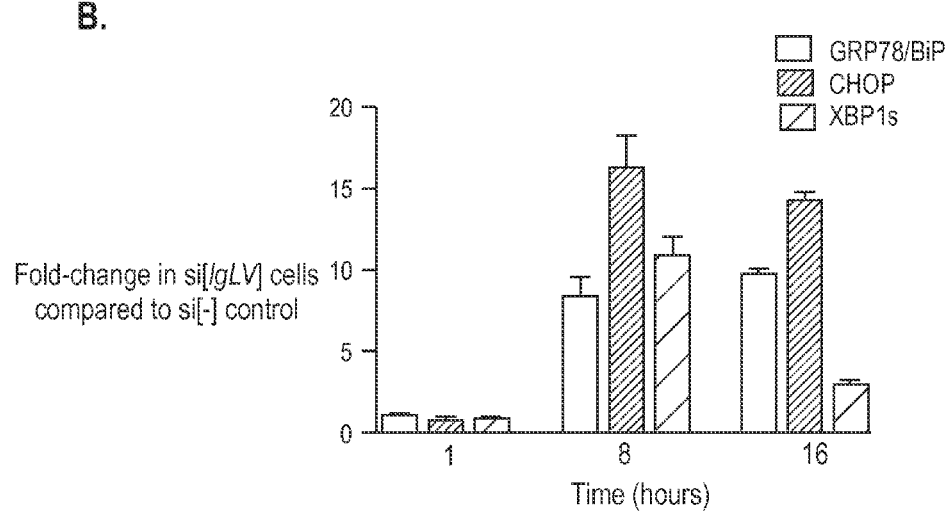
B.

Fig. 13
Light chain knockdown in plasma cells making light and heavy chain causes caspase 3/7 activation and mitochondrial depolarization
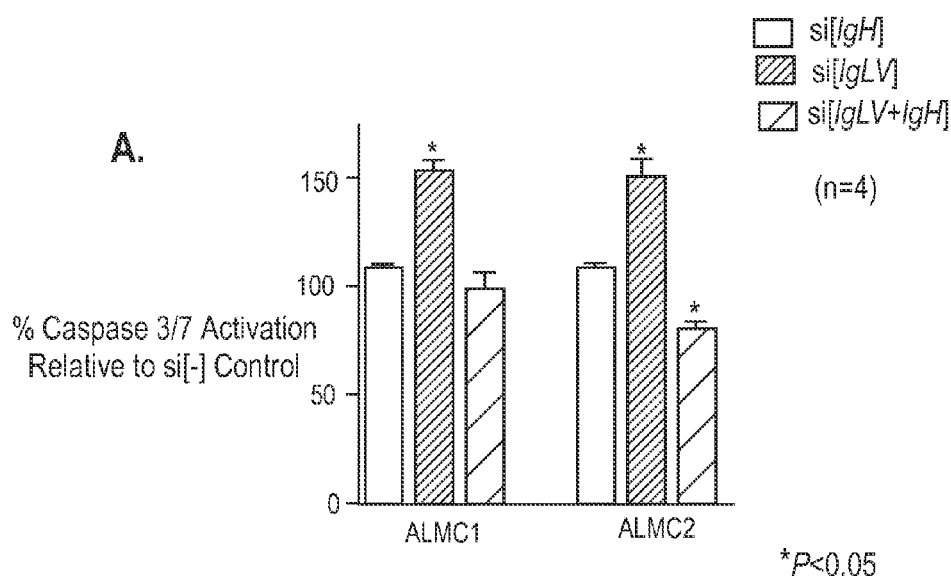
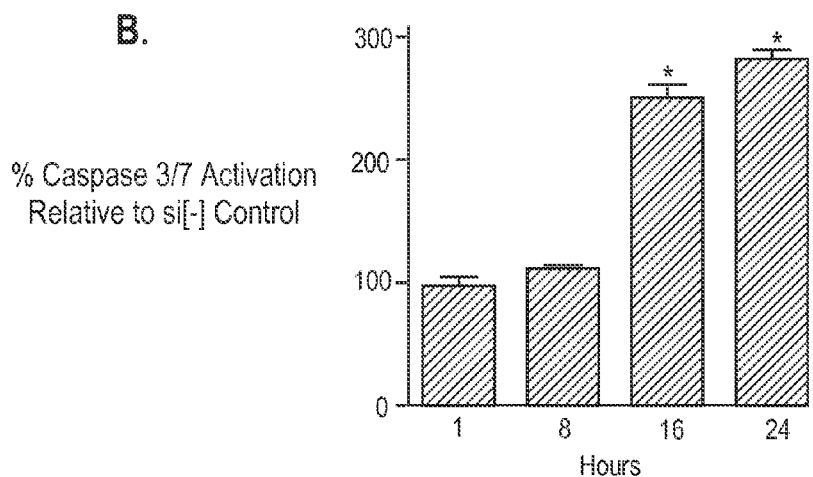

Fig. 13
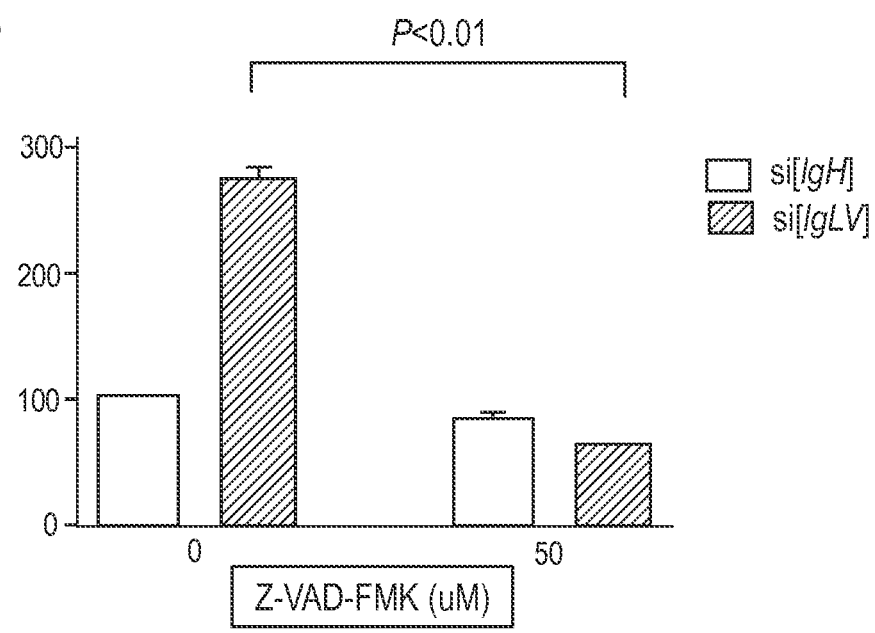
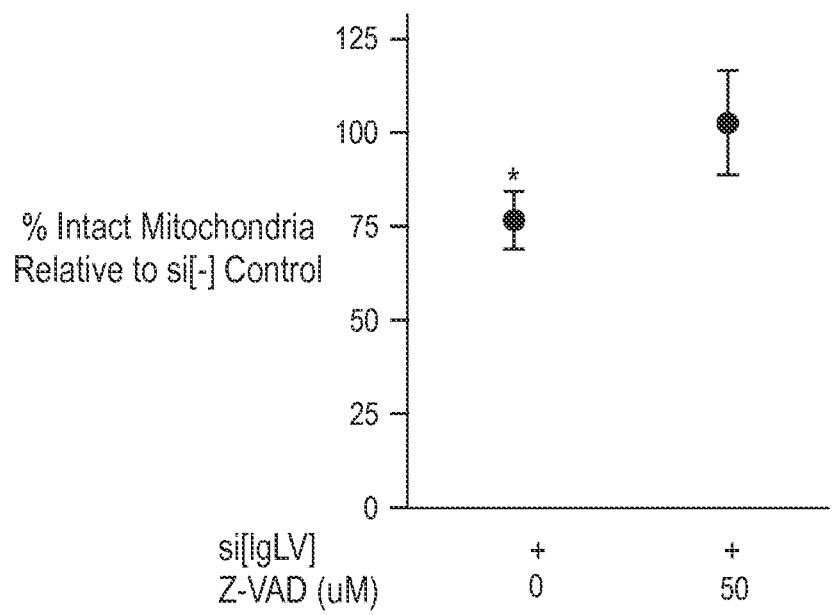

Fig. 14
Light chain knockdown induces caspase-dependent apoptosis in plasma cells making heavy chains
A.
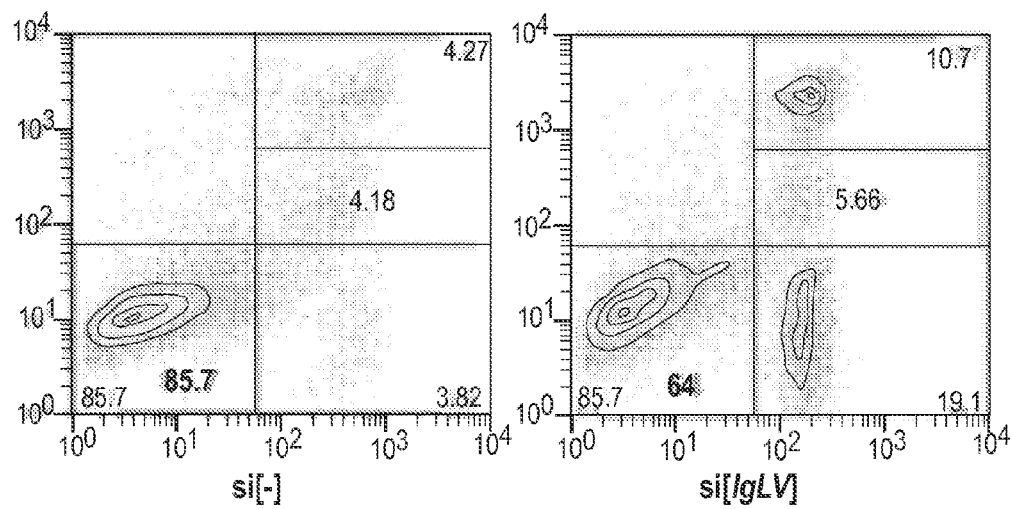
B.
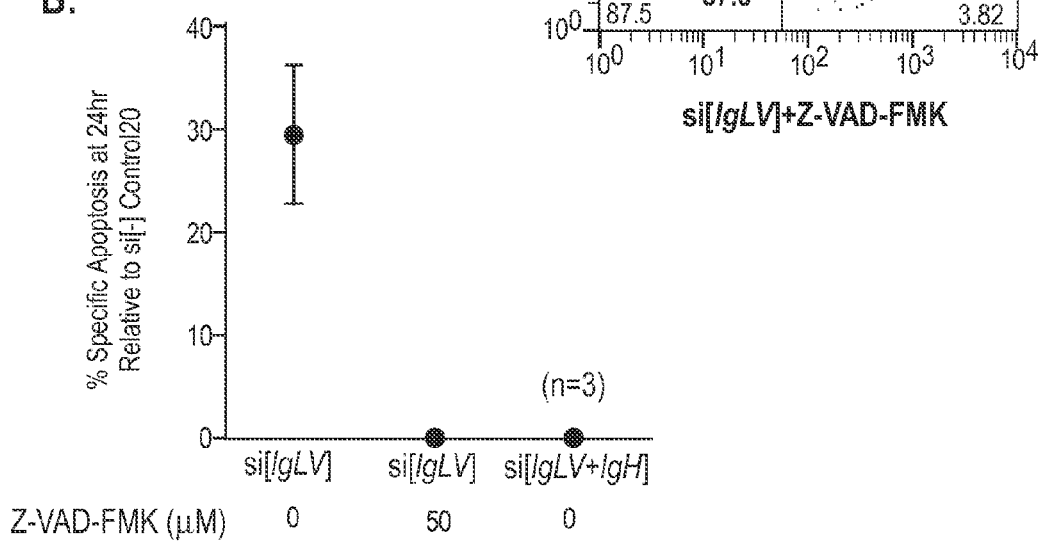

Fig. 15
Light chain knockdown induces cell death in patient plasma cells making heavy chains
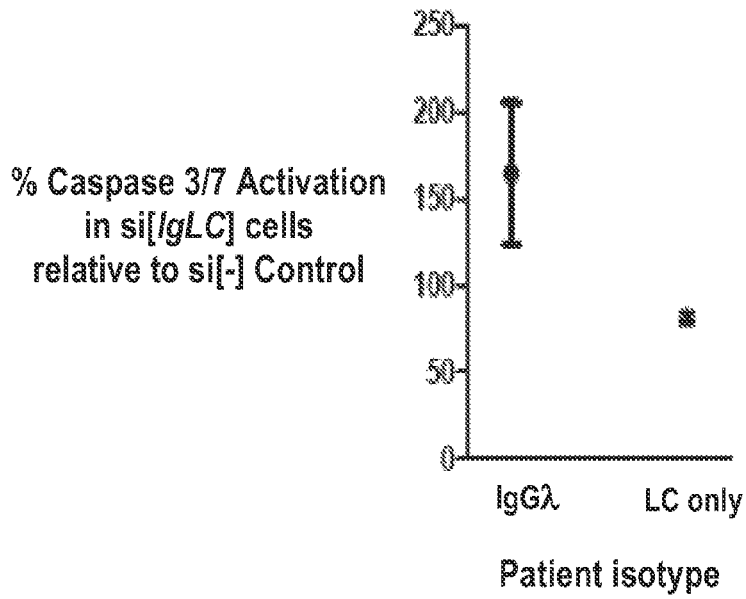
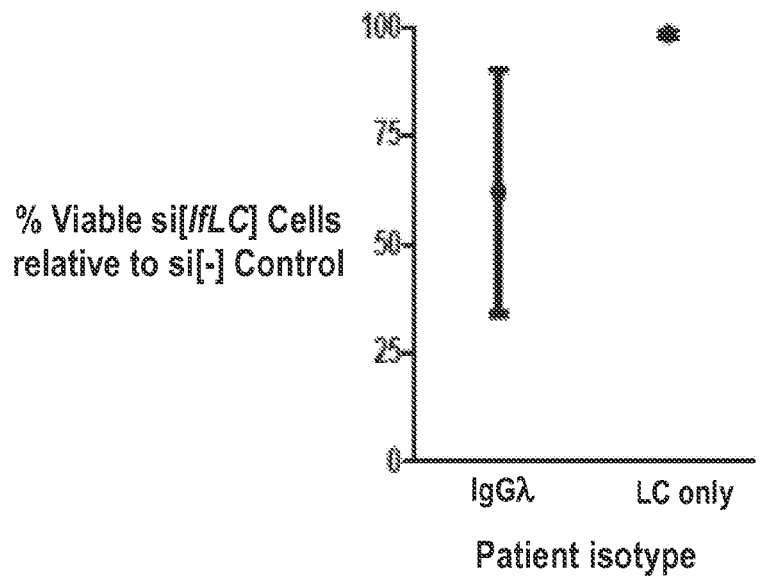

SEQUENCE LISTING

```
<160> NUMBER OF SEQ ID NOS: 24

<210> SEQ ID NO 1
<211> LENGTH: 19
<212> TYPE: RNA
<213> ORGANISM: Homo sapiens

<400> SEQUENCE: 1
ccaaacaaag caacaacaa                                            19

<210> SEQ ID NO 2
<211> LENGTH: 19
<212> TYPE: RNA
<213> ORGANISM: Homo sapiens

<400> SEQUENCE: 2
acgccugagc aguggaagu                                            19

<210> SEQ ID NO 3
<211> LENGTH: 19
<212> TYPE: RNA
<213> ORGANISM: Homo sapiens

<400> SEQUENCE: 3
cuucaagcca acaaggcca                                            19

<210> SEQ ID NO 4
<211> LENGTH: 19
<212> TYPE: RNA
<213> ORGANISM: Homo sapiens

<400> SEQUENCE: 4
ccgugacagu ggccuggaa                                            19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
ccaaacaaag caacaacaa                                            19

<210> SEQ ID NO 6
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 6
uuguuguugc uuuguuugg                                                    19

<210> SEQ ID NO 7
<211> LENGTH: 19
<212> TYPE: RNA
<213> ORGANISM: Artificial Sequence
<220> FEATURE:
<223> OTHER INFORMATION: Synthetic

<400> SEQUENCE: 7
acgccugagc aguggaagu                                                    19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
acuuccacug cucaggcgu                                                    19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
cuucaagcca acaaggcca                                                    19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
uggccuuguu ggcuugaag                                                    19

<210> SEQ ID NO 11
<211> LENGTH: 19
<212> TYPE: RNA
<213> ORGANISM: Artificial Sequence
<220> FEATURE:
<223> OTHER INFORMATION: Synthetic

<400> SEQUENCE: 11
ccgugacagu ggccuggaa                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
```
uuccaggcca cugucacgg                                                    19

<210> SEQ ID NO 13
<211> LENGTH: 25
<212> TYPE: RNA
<213> ORGANISM: Homo sapiens

<400> SEQUENCE: 13
guaacuccca ggagaguguc acaga                                             25

<210> SEQ ID NO 14
<211> LENGTH: 25
<212> TYPE: RNA
<213> ORGANISM: Homo sapiens

<400> SEQUENCE: 14
gcacccugac gcugagcaaa gcaga                                             25

<210> SEQ ID NO 15
<211> LENGTH: 25
<212> TYPE: DNA
<213> ORGANISM: Homo sapiens

<400> SEQUENCE: 15
guggcugcac caucugucuu cauct                                             25

<210> SEQ ID NO 16
<211> LENGTH: 25
<212> TYPE: DNA
<213> ORGANISM: Homo sapiens

<400> SEQUENCE: 16
cuggaacugc cucguugug ugcct                                              25

<210> SEQ ID NO 17
<211> LENGTH: 25
<212> TYPE: RNA
<213> ORGANISM: Artificial Sequence
<220> FEATURE:
<223> OTHER INFORMATION: Synthetic

<400> SEQUENCE: 17
guaacuccca ggagaguguc acaga                                             25

<210> SEQ ID NO 18
<211> LENGTH: 27
<212> TYPE: RNA
<213> ORGANISM: Artificial Sequence
<220> FEATURE:
<223> OTHER INFORMATION: Synthetic

<400> SEQUENCE: 18
ucugugacac ucuccuggga guuaccc                                           27

<210> SEQ ID NO 19
<211> LENGTH: 25
<212> TYPE: RNA
<213> ORGANISM: Artificial Sequence
<220> FEATURE:
<223> OTHER INFORMATION: Synthetic

<400> SEQUENCE: 19
gcacccugac gcugagcaaa gcaga                                             25

```
<210> SEQ ID NO 20
<211> LENGTH: 27
<212> TYPE: RNA
<213> ORGANISM: Artificial Sequence
<220> FEATURE:
<223> OTHER INFORMATION: Synthetic

<400> SEQUENCE: 20
ucugcuuugc ucagcgucag ggugcug                                          27

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
guggcugcac caucugucuu cauct                                            25

<210> SEQ ID NO 22
<211> LENGTH: 27
<212> TYPE: RNA
<213> ORGANISM: Artificial Sequence
<220> FEATURE:
<223> OTHER INFORMATION: Synthetic

<400> SEQUENCE: 22
agaugaagac agauggugca gccacag                                          27

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
cuggaacugc cucuguugug ugcct                                            25

<210> SEQ ID NO 24
<211> LENGTH: 27
<212> TYPE: RNA
<213> ORGANISM: Artificial Sequence
<220> FEATURE:
<223> OTHER INFORMATION: Synthetic

<400> SEQUENCE: 24
aggcacacaa cagaggcagu uccagau                                          27
```

METHODS AND COMPOSITIONS FOR TARGETING IMMUNOGLOBULINS

CROSS REFERENCE TO RELATED APPLICATIONS

This application a national phase application under 35 U.S.C. §371 of PCT International Application No. PCT/US2014/011617, filed on Jan. 15, 2014, which claims priority to U.S. Provisional Patent Application Ser. No. 61/752,721, filed Jan. 15, 2013, each of which are herein incorporated by reference in its entirety.

FIELD OF THE INVENTION

The present invention relates to compositions and methods for targeting immunoglobulins and immunoglobulin-producing plasma cells. In particular, the present invention provides nucleic acid based compounds for targeting immunoglobulins for research, screening, and therapeutic applications.

BACKGROUND OF THE INVENTION

Diseases related to immunoglobulins and immunoglobulin-producing plasma cells include clonal plasma cell dyscrasias and autoimmune diseases.

Plasma cell dyscrasias including but not limited to monoclonal gammopathy of undetermined significance (MGUS), symptomatic and smoldering multiple myeloma, Waldenstrom's macroglobulinemia, and systemic light-chain amyloidosis are derived from a single immortalized founding clone and produce a clonal immunoglobulin protein. Both the immunoglobulin proteins and the clonal plasma cells in these diseases can damage organs such as the heart, kidneys, liver, gastrointestinal tract, bones, immune system, thyroid, soft tissues and peripheral nervous system.

Existing therapies include steroids, toxic chemotherapy agents such as melphalan, adriamycin and cyclophosphamide, as well proteasome inhibitors, immunomodulatory drugs, radiation, and autologous and allogeneic stem cell transplantation. These diseases remain incurable and shorten survival.

Autoimmune diseases arise from an inappropriate immune response of the body against substances and tissues normally present in the body. Autoimmune diseases are characterized by the destruction of one or more types of body tissue, abnormal growth of an organ, or changes in organ function. An autoimmune disorder may affect one or more organ or tissue types. Organs and tissues commonly affected by autoimmune disorders include: blood vessels, connective tissues, endocrine glands such as the thyroid or pancreas, joints, muscles, red blood cells, or skin.

A person may have more than one autoimmune disorder at the same time. Examples of autoimmune (or autoimmune-related) disorders include, but are not limited to, systemic lupus erythematosus, type I diabetes, Addison's disease, celiac disease, dermatomyositis, Graves disease, Hashimoto's thyroiditis, multiple sclerosis, myasthenia gravis, pernicious anemia, reactive arthritis, rheumatoid arthritis, and Sjogren syndrome.

Existing treatments include supplements to replace a hormone or vitamin that the body is lacking (e.g., thyroid supplements, vitamins such as B12, or insulin injections), blood transfusions, and immunosuppressive medicines. Such medicines may include corticosteroids (such as pred-nisone) and nonsteroid drugs such as azathioprine, cyclophosphamide, mycophenolate, sirolimus, or tacrolimus.

Existing treatments can have serious side effects and are not always or often effective. New therapies are needed.

SUMMARY

The present invention relates to compositions and methods for targeting immunoglobulins and immunoglobulin-producing plasma cells. In particular, the present invention provides nucleic acid based compounds for targeting immunoglobulins for research, screening, and therapeutic applications.

Embodiments of the present invention provide compositions, kits, uses, and methods for inhibiting immunoglobulin light chain production in cells for research, screening, and therapeutic uses. In some embodiments, the present invention provides universal siRNA pools that can shut down production of immunoglobulin kappa or lambda chain production without knowledge of the sequence of the particular immunoglobulin. In some embodiments, administration of the compositions results in plasma cell death (e.g., induced by the shutting down of immunoglobulin kappa or lambda light chains). Such compositions and methods find use in screening, research (e.g., in animal models of disease) and therapeutic (e.g., in the treatment of plasma cell mediated or immune disorders).

For example, in some embodiments, the present invention provides a composition comprising a plurality of distinct nucleic acids complementary to an immunoglobulin light chain (e.g., a kappa or lambda light chain) constant region. In some embodiments, the composition comprises sequences (e.g., selected from SEQ ID NOs: 5, 6, 7, 8, 9, 10, 11 or 12). In some embodiments, the nucleic acids are siRNAs having nucleic acid sequences selected from, for example, SEQ ID NOs: 5 and 6; 7 and 8; 9 and 10; or 11 and 12. In some embodiments, the composition comprises at least 4, 6, or all of SEQ ID NOs: 5-12. In some embodiments, the nucleic acids consist essentially of or consist of SEQ ID NOs: 5-12.

In some embodiments, the nucleic acids comprise sequences (e.g., selected SEQ ID NOs: 17, 18, 19, 20, 21, 22, 23, or 24). In some embodiments, the nucleic acids are siRNAs having nucleic acid sequences selected from, for example, SEQ ID NOs: 17 and 18; 19 and 20; 21 and 22; or 23 and 24. In some embodiments, the composition comprises at least 4, 6, or all of SEQ ID NOs: 17-24. In some embodiments, the nucleic acids consist essentially of or consist of SEQ ID NOs: 17-24.

In some embodiments, the composition is a pharmaceutical composition. In some embodiments, the composition further comprises a pharmaceutically acceptable carrier.

Further embodiments provide a kit comprising any of the aforementioned compositions.

Additional embodiments provide the use of any of the aforementioned compositions in the inhibition of immunoglobulin light chain production in a cell. In some embodiments, the cell is a plasma cell and the inhibition causes plasma cell death. In some embodiments, the immunoglobulin light chain is a kappa or lambda light chain. In some embodiments, cell is in a subject (e.g., a human or non-human subject). In some embodiments, the subject exhibits symptoms of a clonal plasma cell dyscrasia or an autoimmune disorder (e.g., a monoclonal or polyclonal antibody-mediated disease). In some embodiments, the use reduces or eliminates symptoms of the dyscrasia or disorder.

In yet other embodiments, the present invention provides a method of inhibiting antibody light chain production in a cell, comprising: contacting a cell with any of the aforementioned compositions.

Additional embodiments are described herein.

BRIEF DESCRIPTION OF THE DRAWINGS

FIG. 8 shows light chain reductions by flow cytometry and immunoblot in H929 myeloma cells after si[IgLC].

FIG. 9 shows flow cytometry with staining for Kappa and Lambda showing effect of combined si[IgLC+IgKC] knockdown in a pool of MM1S and H929 cells at a 1:1 ratio.

FIG. 10 shows that knockdown of lambda light chains leaves unmated heavy chains that associate with GRP78.

FIG. 12 shows the rapid onset of the unfolded protein response after lambda light chain knockdown.

FIG. 13 shows that light chain knockdown in plasma cells making light and heavy chains causes caspase3/7 activation and mitochondrial depolarization.

FIG. 14 shows that light chain knockdown induces caspase-dependent apoptosis in plasma cells making heavy chains after light chain knockdown.

FIG. 15 shows that light chain knockdown induces cell death in patient plasma cells making heavy chains.

DEFINITIONS

Figure 1:
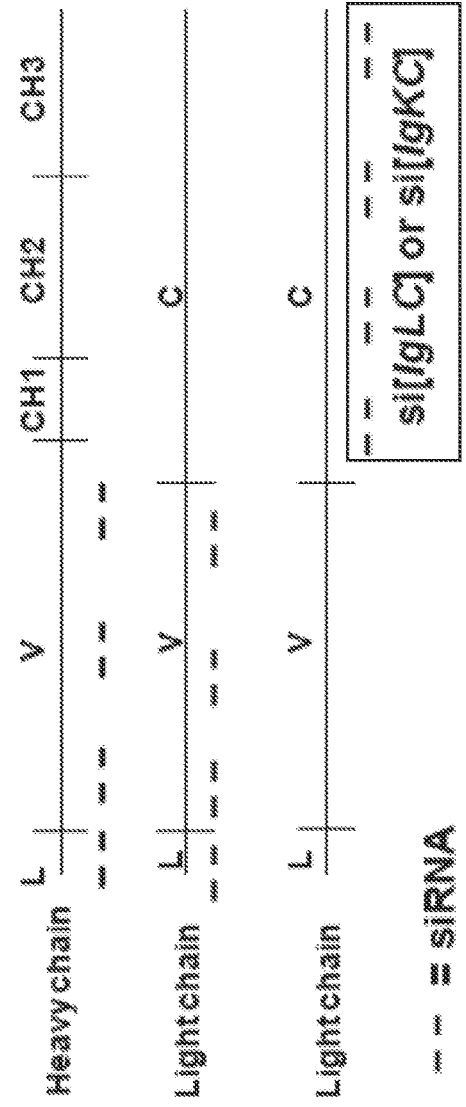
FIG. 1 shows the design of pools of siRNA to knock down immunoglobulin heavy and light chain gene expression in plasma cells.

To facilitate an understanding of the present invention, a number of terms and phrases are defined below.

As used herein, the terms "'small interfering RNA" or "siRNA" refers to double-stranded RNA molecules, comprising a sense strand and an antisense strand, having sufficient complementarity to one another to form a duplex. Such sense and antisense strands each have a region of complementarity ranging, for example, from about 10 to about 30 contiguous nucleotides that base pair sufficiently to form a duplex or double-stranded siRNA. Such siRNAs are able to specifically interfere with the expression of a gene by triggering the RNAi machinery of a cell to remove RNA transcripts having identical or homologous sequences to the siRNA sequence. As described herein, the sense and antisense strands of siRNA may each consist of only complementary regions, or one or both strands may comprise additional sequences, including non-complementary sequences, such 5' and 3' overhangs. In addition, such siRNAs may have other modifications, such as, for example, substituted or engineered nucleotides or other sequences, which contribute to either the stability of the siRNA, its delivery to a cell or tissue, or its potency in triggering RNAi. It is to be understood that the terms "strand" and "oligonucleotide" may be used interchangeably in reference to the sense and antisense strands of siRNA compositions.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by bacterial infection.

The term "diagnosed," as used herein, refers to the recognition of a disease by its signs and symptoms, or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present invention) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art.

In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent (siRNA) with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]). In some embodiments, the carriers include immunoliposomes and nanoparticles.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., induce cell death). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

The present invention relates to compositions and methods for targeting immunoglobulins and immunoglobulin-producing plasma cells. In particular, the present invention provides nucleic acid based compounds for targeting immunoglobulins for research, screening, and therapeutic applications.

The translation of immunoglobulin light chain proteins in plasma cells from the genetic blueprint of messenger RNA can be disrupted and stopped by the introduction of small interfering RNA (siRNA) designed based on common sequences of light chain constant region genes. Embodiments of the present disclosure provide siRNA agents that are degenerate for constant regions of lambda or kappa light chains and stop immunoglobulin light chain production in human plasma cells. Without light chains to form intact antibodies the production of intact antibodies is also stopped. In addition, in plasma cells making intact antibodies with heavy chains and light chains, the lack of light chains not only stops production of light chain and therefore stops production of intact antibodies but it also leaves heavy chains unmated, creates stress in the endoplasmic reticulum, triggers the unfolded protein response and causes apoptosis of the plasma cells. The siRNA agents of embodiments of the present disclosure, then, can perform double duty. They can turn off light chain production and the production of intact antibodies and, in plasma cells making intact antibodies, cause plasma cell death.

Figure 6:
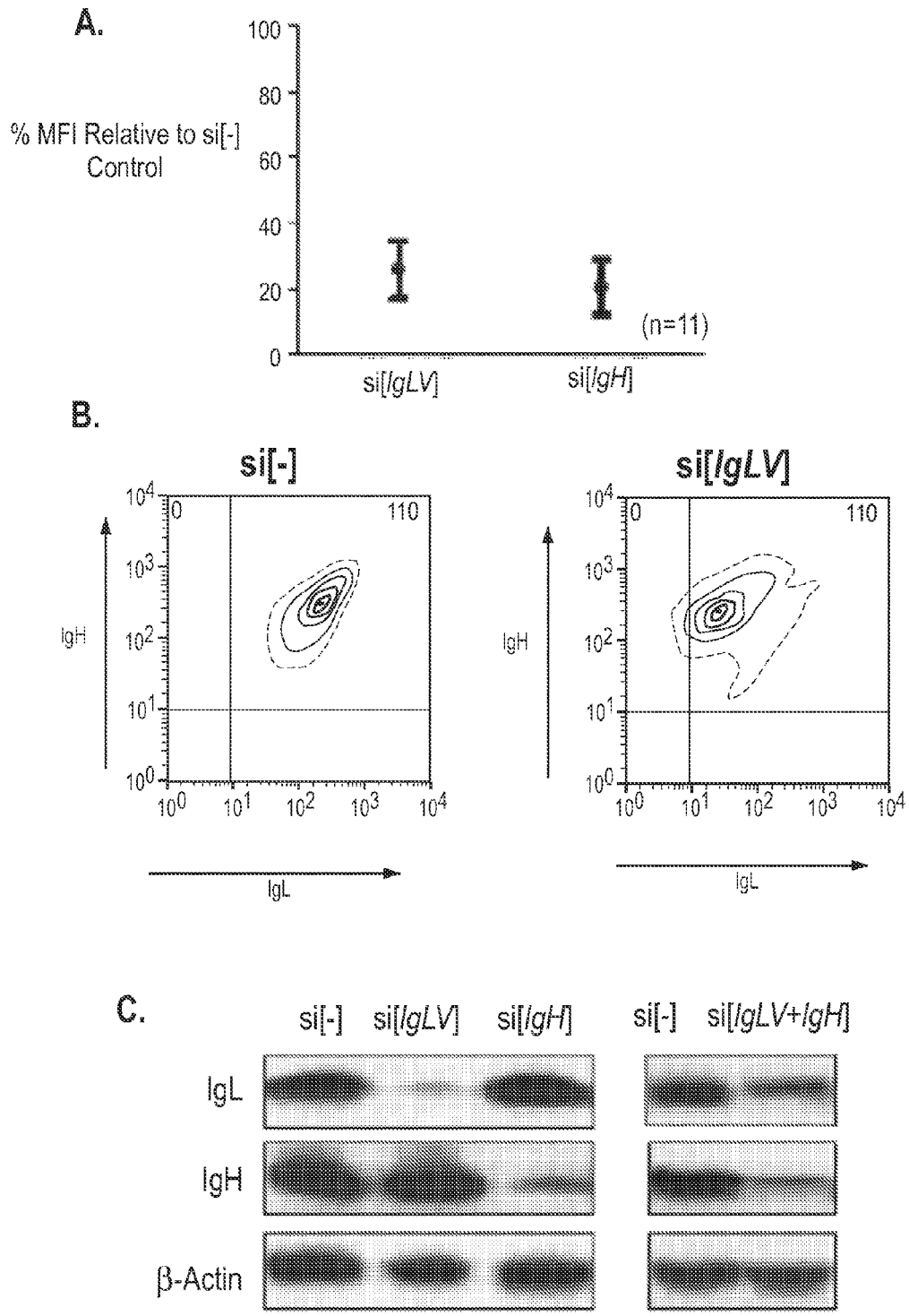
FIG. 6 shows reductions in light and heavy chain proteins with siRNA.

Silencing the genetic message that provides the blueprint for immunoglobulin heavy or light chain production inside of plasma cells is feasible using the hypervariable region sequences as targets as shown in FIG. 6 but the challenge and limitation of such an approach are the specificity and uniqueness of each plasma cell clone and its proprietary immunoglobulin molecule. There would be a different target for each plasma cell or clone of plasma cells.

In clonal plasma cell dyscrasias such as multiple myeloma or systemic light-chain amyloidosis the plasma cells are derived from a single founding clone and therefore these diseases and others such as monoclonal gammopathy of undetermined significance (MGUS) or Waldenstrom's macroglobulinemia are called monoclonal gammopathies. The bases for monoclonality are the processes of immunoglobulin gene re-arrangement and somatic hypermutation that provide the B-cell lineage and humoral immune system with diversity of repertoire. These processes allow a normal B cell, for example, after activation or vaccination, to mature and differentiate into a plasma cell that produces a unique antibody specific for an immunogenic aspect or epitope of the target protein. Antibodies are globular proteins that have unique sequences and shapes allowing them to interact directly with their epitopes. An antibody fits its specific target like a lock fits a key. All complete antibodies (or intact immunoglobulins) have two parts that are joined together inside of plasma cells before being secreted into the extracellular space. These two parts, the heavy and light chains, mate in the endoplasmic reticulum, the factory where all proteins are manufactured. The combination of heavy and light chains gives antibodies their specific and unique sequences and shapes and their affinity for their targets.

The uniqueness of an antibody resides in the series of amino acids in the hypervariable regions, regions that derive initially from variable (V), diversity (D) (in heavy chains) and joining (J) region gene families; individual genes from these families are selected during B cell maturation with loss of other genes of the same families through a process of looping and clipping of DNA, and then these selected or re-arranged genes undergo mutation when B cells are activated in the germinal centers of lymph nodes during an immune response (Raghavan et al., J Biol Chem. 2001; 276:29126-29133; Dudley et al., Adv Immunol. 2005; 86:43-112). During the immune response of antigen encounter and B cell activation in lymph nodes, the nucleotide sequences that encode the light and heavy chain variable regions mutate in a process of affinity maturation, enhancing the antigen-binding activity of the nascent antibody and enabling the germinal center B cells whose antibodies have the best binding affinity to survive, expand, become plasmablasts and home to the bone marrow as plasma cells or continue in the circulation as memory B cells awaiting re-activation (Iwakoshi et al., Nat Immunol. 2003; 4:321-329). Plasmablasts circulate for days producing antibodies and then find niches in the bone marrow where they nest, proliferate in a limited fashion, and continue antibody production for varying lengths of time. Memory B cells circulate in the blood and are subject to re-activation and differentiation into plasmablasts. The germinal center experience is critical for B cell expansion and differentiation into antibody producing plasma cells.

In addition to V, D and J regions, immunoglobulin light and heavy chains also have structural or constant regions (Bellotti et al., Biochim Biophys Acta. 1996; 1317:161-167). The constant regions of heavy chains are complex while those of light chains are limited in number and have few polymorphic or mutational differences. Direct interference with heavy or light chain production is feasible by employing siRNA designed specifically for a plasma cell's heavy or light chain variable region mRNA sequence as indicated in FIG. 1. Because of the unique or hypervariable character of these regions, such an approach utilizes the design of a specific siRNA to silence the production of the light or heavy chain in each cell, a challenging prospect both in patients with monoclonal gammopathies and in patients with autoreactive polyclonal antibody-mediated diseases such as systemic Lupus erythematosis or autoimmune hemolytic anemia (Gu et al., Contrib Nephrol. 2007; 153:156-181). In effect, for siRNA directed at the variable region gene sequences to work in patients with immunoglobulin-related disease, each patient would need a unique siRNA to stop light or heavy chain production of each clone of plasma cells. The compositions and methods of embodiments of the present disclosure solve this problem by using consensus sequences within immunoglobulin light chain constant region mRNA to design siRNAs (e.g., the si[IgLC] and si[IgKC] siRNA), creating agents that are universal and can be used to silence light chain production and disrupt production of intact antibodies without regard for the uniqueness of the immunoglobulin sequences. Furthermore, in plasma cells making both light and heavy chains, direct interference with production of light chains causes plasma cell death because of the burden of unmated heavy chains in the endoplasmic reticulum. Unmated heavy chains trigger the unfolded protein response and lead to caspase-dependent apoptosis as shown in FIGS. 10 through 15.

Heavy chains have a hydrophobic domain (CH1) where the chaperone GRP78 binds until GRP78 is displaced, in the normal course of antibody production, by a mating light chain (Feige et al., Mol Cell. 2009; 34:569-579). GRP78 is also known as the heavy chain binding protein (BiP), is a member of the hsp70 family, and is an important, abundant and multi-functional protein in the endoplasmic reticulum (ER) with numerous substrate-and-partner associations. Like other hsp70 chaperones, it binds to hydrophobic sites in unfolded polypeptides, regulating their folding and post-translational modifications in an ATP-dependent manner. In plasma cells, GRP78 works with co-chaperones to enable heavy and light chains to mate in the ER prior to intact antibody secretion. GRP78 is also a central player in the unfolded protein response (UPR) because it modulates the activation of the three ER sensors that control the UPR: IRE1α (inositol requiring enzyme 1 alpha) which has both kinase and endoribonuclease domains, can bind TRAF2 and activate JNK; ATF6 (activating transcription factor 6), a basic leucine zipper protein whose cleaved form up-regulates expression of genes for ER chaperones (GRP78, GRP94) and for the transcription factor XBP1 which is then cleaved by activated IRE1α to a highly active spliced form (XBP1s); and PERK (PKR-like ER kinase) that phosphorylates eIF2α to inactivate it and reduce ER protein load, up-regulates expression of a transcription factor (CHOP) that may suppress Bcl-2, increase Bim and activate Nrf-2, enhancing the transcription of proteasome subunit genes.18 In many cell types the UPR has been shown to possess a pattern of sequential timing in which, as cells respond to ER-stress, ER-based signals first aim to restore homeostasis and promote survival but then, if the stress is prolonged or overwhelming, trigger apoptosis. The UPR in plasma cells is more complex than in cell types that are not professional secretory cells in part because of the multiple roles of GRP78.

Unlike light chains without heavy chains, heavy chains without light chains are not secretory competent because of the unstable CH1 region. They misfold and accumulate within the cell. With RNA interference reducing light chain production in the ER, the burden of misfolded heavy chains triggers the UPR and results in increased production of GRP78 to bind the unmated heavy chains. The sequence of events after that reflects a fundamental theme in plasma cell biology—that unmated heavy chains are toxic to plasma cells. Therefore, an excess of unmated heavy chains triggers the UPR, causing overwhelming ER stress and apoptosis in plasma cells with an excess of unmated heavy chains.

For example, light-chain-deficient mice attain a complete block in B cell development at the stage when light-chain rearrangement should occur, resulting in surface immunoglobulin M deficiency, retention of unmated heavy chains in the cytoplasm, dramatic overall reduction in B cells, lack of plasma cells and no response to immunizations (Zou et al., J Immunol. 2003; 170:1354-1361). Furthermore, normal human plasma cells make more light than heavy chains, probably to minimize intracellular accumulation of unmated heavy chains in the E R (Katzmann J A, Clark R J, Abraham R S, et al. Serum reference intervals and diagnostic ranges for free kappa and free lambda immunoglobulin light chains: relative sensitivity for detection of monoclonal light chains. Clin Chem. 2002; 48:1437-1444). And hybridomas, immortalized cell lines derived from the fusion of B cells and non-secretory murine myeloma cells, are created in order to produce monoclonal antibodies whose specificity is endowed by the B-cell heavy and light chain genes and, after passage in culture, often lose heavy chain production and make only light chains (Haas I G, Wabl M R. Immunoglobulin heavy chain toxicity in plasma cells is neutralized by fusion to pre-B cells. Proc Natl Acad Sci USA. 1984; 81:7185-7188). Rarely does the opposite occur. Moreover, 20% of human myelomas make only light chains, 80% make a complete antibody and vanishingly few make heavy chains only—and the rare heavy chain myelomas lack the CH1 region that causes instability (Palumbo et al., N Engl J Med. 2011; 364:1046-1060).

The siRNA agents described in embodiments of the present invention turn off light chain production with no need for a priori gene sequencing for each clone's hypervariable region. This capacity addresses the problem of the uniqueness of each plasma cell clone's antibody. By using consensus sequences in the immunoglobulin light chain constant region, sequences that are specific to all light chains of that isotype, light chain production is stopped, thereby also halting production of the intact immunoglobulin. In addition, these agents can also cause plasma cell apoptosis in clones making intact immunoglobulins because of the toxicity of unmated heavy chain molecules. Apoptosis occurs because the terminal unfolded protein response is activated by the association between unmated heavy chains and the chaperone GRP78 in the endoplasmic reticulum (Jager et al., Biol Cell. 2012; 104:259-270). The double duty capacity of these agents is most relevant in the context of the production of harmful monoclonal light chains or antibodies in monoclonal gammopathies and in polyclonal autoantibody-mediated autoimmune diseases.

I. Compositions

As described herein, embodiments of the present invention provides compositions, systems, kits, and methods for inhibiting antibody light chain production in a cell (e.g., siRNAs).

RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins.

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

In some embodiments, the present invention utilizes siRNA including blunt ends (See e.g., US20080200420, herein incorporated by reference in its entirety), overhangs (See e.g., US20080269147A1, herein incorporated by reference in its entirety), locked nucleic acids (See e.g., WO2008/006369, WO2008/043753, and WO2008/051306, each of which is herein incorporated by reference in its entirety). In some embodiments, siRNAs are delivered via gene expression or using bacteria (See e.g., Xiang et al., Nature 24: 6 (2006) and WO06066048, each of which is herein incorporated by reference in its entirety).

Chemical modifications can enhance the stability and uptake of naked siRNAs (Choung et al., Biochem Biophys Res Commun. 2006; 342(3):919-927.) siRNAs can be directly modified without impacting their ability to silence their targets. Chemical modifications have been rigorously investigated for virtually every part of siRNA molecules, from the termini and backbone to the sugars and bases, with the goal of engineering siRNA with prolonged half-life and increased cellular uptake. In some embodiments, the sugar moiety is modified. For example, the incorporation of a 2'-fluoro (2'-F), 2'-O-methyl, 2'-halogen, 2'-amine, or 2'-deoxy (Kawasaki et al., J Med Chem. 1993; 36(7):831-841; Rusckowski et al., Antisense Nucleic Acid Drug Dev. 2000; 10(5):333-345; Pieken et al., Science. 1991; 253(5017):314-317; Parrish et al., Mol Cell. 2000; 6(5):1077-1087) can significantly increase the stability of siRNA in serum, as can the bridging of the sugar's 2'- and 4'-positions with a —O—CH2 linker (producing what is called a "locked nucleic acid" or LNA) (Elmen et al., Nucleic Acids Res. 2005; 33(1):439-447). The 2'-F can be introduced through endogenous transcription as opposed to chemical synthesis. In some embodiments, 2'-O-methyl modification of only the sense strand is utilized (Chen et al., RNA. 2008; 14(2):263-274).

In some embodiments, the present invention provides pools of degenerate siRNAs (e.g., those described in Tables 1 and 3) that universally inhibit production of kappa or lambda light chains. The present invention is not limited to particular compositions. Examples include, but are not limited to the nucleic acids described by SEQ ID NOs: 5-12 or 17-24. In some embodiments, compositions include 2, 4, 6 or all of SEQ ID NOs: 5-12 and/or 17-24. In some embodiments, nucleic acids consist essentially of or consist of the nucleic acids of SEQ ID NOs: 5-12 and 17-24.

In some embodiments, one or more (e.g., 1, 2, 3, 4, or more) nucleotides of SEQ ID NOs: 5-12 and 17-24 are altered, substituted, or modified, so long as the properties of the nucleic acids are maintained (e.g., inhibiting expression of antibody light chains).

For example, embodiments of compositions of the present invention may comprise an siRNA comprising a sense RNA sequence and an antisense RNA sequence, wherein sense RNA sequence of siRNA may be at least about 70%, 80%, 90%, 95%, 96%, 97%, 98% 98%, 99%, or more homologous to the described sequences with antisense RNA sequence complementary to such sense RNA sequence (e.g., able to hybridize to the sense RNA sequence at a physiological temperature). However, the degree of homology between sense strand of siRNA and the antisense strand may be higher, such as, for example, at least about 80%, 90%, 95%, or 100% homologous or identical, with antisense strand complementary thereto.

In some embodiments, the present invention provides kits comprising the aforementioned compositions and one or more additional components useful, necessary, or sufficient for using the kits (e.g., delivery systems, etc.).

II. Uses

In some embodiments, the present invention provides compositions and methods for inhibiting the production of antibody lights chains in cells. Is some embodiments, the methods provide research or screening uses in animals (e.g., screening compounds in animal models of immune diseases and research into immune diseases.

In some embodiments, the present invention provides therapeutic methods. For example, in some embodiments, the compositions described herein find use in treating diseases of clonal plasma cells (e.g., by inhibiting antibody production or inducing plasma cell death) or autoimmune disorders. For example, in some embodiments, the compositions described herein find use in treating subjects with clonal plasma cell diseases and with autoimmune diseases in which autoreactive antibodies play a role.

Examples of clonal plasma cell diseases include, but are not limited to: monoclonal gammopathy of undetermined significance (MGUS), smoldering multiple myeloma, symptomatic multiple myeloma, systemic light-chain amyloidosis, monoclonal immunoglobulin deposition disorder, light-chain deposition disease, immunotactoid glomerulonephritis, Waldenstrom's macroglobulinemia, scleromyxedema, cryoglobulinemia, POEMS (Polyneuropathy, Organomegaly, Monoclonal protein, Skin changes), and TEMPI (Telangectasias, Erythrocytosis, Monoclonal protein, Perinephric fluid collection, Intrapulmonary shunting).

Example of autoimmune disorders include, but are not limited to: systemic lupus erythematosus, type I diabetes, Addison's disease, celiac disease, dermatomyositis, Graves disease, Hashimoto's thyroiditis, multiple sclerosis, myasthenia gravis, pernicious anemia, reactive arthritis, rheumatoid arthritis, Sjogren syndromesystemic lupus erythematosus, polyarteritis nodosa, Goodpasture's syndrome, autoimmune hemolytic anemia, and immune thrombocytopenic purpura.

In some embodiments of the present invention, the compositions are administered alone, while in some other embodiments, the compositions are preferably present in a pharmaceutical formulation comprising at least one active ingredient/agent (e.g., siRNA), as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Delivery of siRNAs to plasma cells in the blood, lymphatics, spleen, bone marrow and other sites in vivo is described e.g., (Hovey et al., Gene Ther. 2011; 18:1150-1156; Rodriguez et al. Antisense Nucleic Acid Drug Dev. 2002; 12:311-325; Gao et al., Biomaterials. 2012; 33:270-282; Gao et al., Biomaterials. 2011; 32:3459-3470; Petrocca et al., J Clin Oncol. 2011; 29:747-754; each of which is herein incorporated by reference in its entirety).

In embodiments of the methods of the present invention, the siRNA is administered to an individual, subject, or patient either as a naked siRNAs or as part of a recombinant plasmid or vector expressing such siRNAs, which may also be delivered in conjunction with a delivery reagent. Alternatively, embodiments of the siRNA compositions of the present invention may be administered as a viral vector(s) encoding either separate sense and antisense siRNA. When naked siRNAs, or recombinant plasmids or vectors expressing a siRNA are administered directly to cells, such delivery may be achieved, for example, by electroporation, gene gun, microinjection, or complex formation with synthetic carriers (such as lipids, polymers, and/or peptides). In addition, embodiments of the siRNAs are delivered as a pharmaceutical composition in combination with a pharmaceutically acceptable carrier.

Suitable delivery reagents for administration in conjunction with the siRNA may include cationic polymers and lipids as well as encapsulated lipid particles, such as liposomes, etc. Examples may include Mirus Transit TKO lipophilic reagent, lipofectin, lipofectamine, cellfectin, or polycations (e.g., polylysine), or liposomes. For further discussion of effective delivery reagents that may be used in combination with present siRNA compositions, see, e.g., De Paula, D. et al. "Hydrophobization and bioconjugation for enhanced siRNA delivery and targeting," RNA 13:431-56 (2007); and Kim, D. et al., "RNAi mechanisms and applications," Biotechniques 44(5):613-16 (2008), the entire disclosures and contents of which are hereby incorporated by reference.

According to some embodiments, the delivery reagent may be a liposome. Liposomes may be used to aid in the delivery of the siRNA to a particular tissue, and can also increase the blood half-life of the siRNA. The selection of lipids is generally guided by consideration of factors such as the desired liposome size and half-life of the liposomes in the blood stream. Methods for the preparation of liposomes as delivery agents that may be used in combination with embodiments of compositions and methods of the present invention are well known in the art. For example, see Szoka et al., "Comparative properties and methods of preparation of lipid vesicles (liposomes)," Ann. Rev. Biophys. Bioeng. 9:467 (1980); Immordino, M. L., "Stealth liposomes: review of the basic science, rationale, and clinical applications, existing and potential," Int. J. Nanomedicine 1(3):297-315 (2006); Samad, A, "Liposomal Drug Delivery Systems: An Update Review," Current Drug Delivery 4(4):297-305 (2007); and U.S. Pat. Nos. 4,235,871, 4,501,728, 4,837,028, and 5,019,369, the entire disclosures and contents of which are hereby incorporated by reference.

The liposomes encapsulating the siRNA may also be modified so as to avoid clearance by the mononuclear macrophage and reticuloendothelial systems, for example by having opsonization-inhibition moieties bound to the surface of the structure. In one embodiment an embodiment of a liposome of the present invention may comprise both opsonization-inhibition moieties and a ligand. Opsonization-inhibiting moieties for use in preparing the embodiment of the liposomes of the present invention may be large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016. Liposomes modified with opsonization-inhibition moieties thus remain in the circulation much longer than unmodified liposomes and are sometimes called "stealth" liposomes.

Opsonization-inhibiting moieties suitable for modifying liposomes are generally water-soluble polymers with a number-average molecular weight from about 500 to about 40,000 daltons, and more preferably from about 2,000 to about 20,000 daltons. Such polymers may include polyethylene glycol (PEG) or polypropylene glycol (PPG) derivatives; e.g., methoxy PEG or PPG, and PEG or PPG stearate synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, may also be suitable. In addition, the opsonization inhibiting polymer may be a block copolymer of PEG and either a polyamino acid, polysaccharide, polyamidoamine, polyethyleneamine, or polynucleotide. The opsonization-inhibiting polymers may also be natural polysaccharides containing amino acids or carboxylic acids, e.g., galacturonic acid, glucuronic acid, mannuronic acid, hyaluronic acid, pectic acid, neuraminic acid, alginic, acid, carrageenan; aminated polysaccharides or oligosaccharides (linear or branched); or carboxylated polysaccharides or oligosaccharides, e.g., reacted with derivatives of carbonic acids with resultant linking of carboxylic groups. For example, the opsonization-inhibiting moiety may be a PEG, PPG, or derivatives thereof. Liposomes modified with PEG or PEG-derivatives are sometimes called "PEGylated liposomes."

The opsonization-inhibiting moiety may be bound to the liposome membrane by any one of numerous well-known techniques. For example, an N-hydroxysuccinimide ester of PEG may be bound to a phosphatidyl-ethanolamine lipid-soluble anchor and then bound to a membrane. Similarly, a dextran polymer may be derivatized with a stearylamine lipid-soluble anchor via reductive amination using Na(CN)BH3 and a solvent mixture such as tetrahydrofuran and water in a 30:12 ratio at 60° C.

The vector containing the appropriate DNA sequence as described herein, as well as an appropriate promoter or control sequence, may be employed to transform an appropriate host to permit the host to express the siRNA. Appropriate cloning and expression vectors for use with prokaryotic and eukaryotic hosts have been described and are well known in the art. See, e.g., Sambrook, et al., Molecular Cloning: A Laboratory Manual, (Second Edition, Cold Spring Harbor, N.Y. 1989). In one embodiment, the cells used to produce the siRNAs are HEK 293T cells.

siRNA compositions may also be delivered using viral vectors by modifying methods generally known in the art. Examples of viral vectors that may be suitable for use with embodiments of methods of the present invention may include retroviral, adenoviral, and adeno-associated viral vectors. Any viral vector capable of encoding or accepting coding sequences for a siRNA to be expressed may be used including, for example, vectors derived from adenovirus (AV), adeno-associated virus (AAV), retroviruses (e.g., lentiviruses), Rhabdoviruses, herpes virus, etc. According to some preferred embodiments, viral vectors that may be used to deliver embodiments of siRNA compositions of the present invention may include lentiviruses or lentiviral-derived vectors. The tropism of the viral vectors may also be modified by pseudotyping the vectors with envelope proteins or other surface antigens from other viruses. For example, an AAV vector of the invention may be pseudotyped with surface proteins from vesicular stomatitis virus (VSV), rabies, Ebola, Marburg, and the like. According to some embodiments, siRNAs is expressed using RNA polymerase III promoters, such as U6, H1, or tRNA promoters.

For further review and discussion of viral vectors see, e.g., De Paula, D. et al., "Hydrophobization and bioconjugation for enhanced siRNA delivery and targeting," RNA 13:431-56 (2007) and Kim, D. et al., "RNAi mechanisms and applications," Biotechniques 44(5):613-16 (2008), the entire disclosures and contents of which are hereby incorporated by reference.

Suitable enteral administration routes for administering embodiments of siRNA compositions include oral, rectal or intranasal delivery. Suitable parenteral administration routes may include intravascular administration (e.g., intravenous bolus injection, intravenous infusion, intra-arterial bolus injection, intra-arterial infusion and catheter instillation into the vasculature); peri- and intra-tissue administration), subcutaneous injection or deposition including subcutaneous infusion (such as by osmotic pumps), direct application to the area at or near a site of infection or risk of infection (e.g., by a catheter or other placement device), and inhalation.

The embodiments of siRNA compositions may be formulated as a pharmaceutical composition in combination with a pharmaceutically acceptable carrier according to techniques known in the art. Embodiments of pharmaceutical compositions of the present invention may be characterized as being sterile and pyrogen-free. Methods for preparing embodiments of pharmaceutical compositions of the present invention are well within the skill in the art, for example as described in Remington's Pharmaceutical Science, (17th ed., Mack Publishing Company, Easton, Pa., 1985); Goodman & Gillman's: The Pharmacological Basis of Therapeutics (11th Edition, McGraw-Hill Professional, 2005); and Griffin P. et al. The Textbook of Pharmaceutical Medicine (Blackwell Publishing, Malden, Mass., 2006), the entire disclosures and contents of which are hereby incorporated by reference.

The present pharmaceutical formulations may comprise a siRNA (e.g., 0.1 to 90% by weight), or a physiologically acceptable salt thereof, mixed with a pharmaceutically acceptable carrier. Physiologically acceptable carriers may include water, buffered water, saline solutions (e.g., normal saline or balanced saline solutions such as Hank's or Earle's balanced salt solutions), 0.4% saline, 0.3% glycine, hyaluronic acid, etc.

Embodiments of pharmaceutical compositions of the present invention may be administered orally, nasally, parenterally, intrasystemically, intraperitoneally, topically (as by drops or transdermal patch), bucally, or as an oral or nasal spray.

An embodiment of a pharmaceutical composition of the present invention for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, etc.), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

Injectable depot forms may be made by forming microencapsule matrices of the siRNA in biodegradable polymers such as polylactide-polyglycolide. Depending upon the ratio of drug to polymer and the nature of the particular polymer employed, the rate of release may be controlled. Examples of other biodegradable polymers may include poly(orthoesters) and poly(anhydrides). Depot injectable formulations may also prepared by entrapping the siRNA, composition in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

In some cases, to prolong the effect of siRNAs it is desirable to slow the absorption from subcutaneous or intramuscular injection. This may be accomplished by the use of a liquid suspension of crystalline or amorphous material with poor water solubility. The rate of absorption of the composition may then depend upon its rate of dissolution which, in turn, may depend upon crystal size and crystalline form. Alternatively, delayed absorption of a parenterally administered form may be accomplished by dissolving or suspending the drug in an oil vehicle. Prolonged absorption of the injectable pharmaceutical composition may be brought about by the inclusion of agents which delay absorption such as aluminum monostearate and gelatin.

Solid dosage forms for oral administration may include, but are not limited to, capsules, tablets, pills, powders, and granules. In such solid dosage forms, the composition of the present invention may be mixed with at least one pharmaceutically acceptable excipient or carrier, such as sodium citrate or dicalcium phosphate and/or: (a) fillers or extenders such as starches, lactose, sucrose, glucose, mannitol, and silicic acid; (b) binders such as, for example, carboxymethylcellulose, alginates, gelatin, polyvinylpyrrolidone, sucrose, and *acacia*; (c) humectants such as glycerol; (d) disintegrating agents such as agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents such as, for example, acetyl alcohol and glycerol monostearate; (h) absorbents such as kaolin and bentonite clay; and/or (i) lubricants such as talc, calcium stearate, magnesium stearate, solid polyethylene glycols, sodium lauryl sulfate, and mixtures thereof. In the case of capsules, tablets and pills, the dosage form can also comprise buffering agents. Soft and hard filled gelatin capsules may also be used excipients, such as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and may also be of a composition that they release the active ingredient(s) only, or preferentially, in a certain part of the intestinal tract, optionally, in a delayed manner. Examples of embedding compositions which may be used may include polymeric substances and waxes.

The embodiments of the pharmaceutical compositions of the present invention may also be in micro-encapsulated form, if appropriate, with one or more of the above-mentioned excipients.

Liquid dosage forms for oral administration may include, but are not limited to, pharmaceutically acceptable emulsions, solutions, suspensions, syrups and elixirs. Liquid dosage forms may contain inert diluents commonly used in the art such as, for example, water or other solvents, solubilizing agents and/or emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions may also include adjuvants such as wetting agents, emulsifying and suspending agents, sweetening, flavoring, or perfuming agents. Suspensions may contain suspending agents, such as ethoxylated isostearyl alcohols, polyoxyethylene sorbitol and sorbitan esters, microcrystalline cellulose, aluminum metahydroxide, bentonite, agar-agar, and/or tragacanth, and mixtures thereof.

Alternatively, the composition may be pressurized and contain a compressed gas, such as nitrogen or a liquefied gas propellant. The liquefied propellant medium and indeed the total composition may preferably be such that the composition does not dissolve therein to any substantial extent. The pressurized composition may also contain a surface active agent. The surface active agent may be a liquid or solid nonionic surface active agent or may be a solid anionic surface active agent. It would be generally preferred that the solid anionic surface active agent be in the form of a sodium salt.

Embodiments of the pharmaceutical compositions of the present invention may also comprise conventional pharmaceutical excipients and/or additives. Suitable pharmaceutical excipients may include stabilizers, antioxidants, osmolality adjusting agents, buffers, and/or pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), and/or, optional additions of calcium or sodium salts (for example, calcium chloride, calcium ascorbate, calcium gluconate or calcium lactate).

Pharmaceutical compositions comprising an embodiment of a siRNA of the present invention may include penetration enhancers to enhance their delivery, such as through the alimentary route. Penetration enhancers may be classified as belonging to one of five broad categories, e.g., fatty acids, bile salts, chelating agents, surfactants and non-surfactants (Lee et al., Critical Reviews in Therapeutic Drug Carrier System, 8:91-192 (1991); Muranishi, Critical Reviews in Therapeutic Drug Carrier Systems, 7:1-33 (1990)). One or more penetration enhancers from one or more of these broad categories may be included. Various fatty acids and their derivatives which act as penetration enhancers may include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). See, e.g., Lee et al., Critical Reviews in Therapeutic Drug Carrier Systems, page 92 (1991); Muranishi, Critical Reviews in Therapeutic Drug Carrier Systems, 7:1 (1990); El-Hariri et al., The mitigating effects of phosphatidylcholines on bile salt- and lysophosphatidylcholine-induced membrane damage," J. Pharm. Pharmacol. 44:651-654 (1992)).

Chelating agents may include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, page 92 (1991); Muranishi, Critical Reviews in Therapeutic Drug Carrier Systems, 7:1 (1990); Buur et al., J. Control Rel., 14:43-51 (1990)). Chelating agents may have the added advantage of also serving as DNase inhibitors.

Surfactants may include, for example, sodium lauryl sulfate, polyoxyethylene-9-lauryl ether and polyoxyethylene-20-cetyl ether (Lee et al., Critical Reviews in Therapeutic Drug Carrier Systems, page 92 (1991)); and perfluorochemical emulsions, such as FC43 (Takahashi et al., J. Pharm. Phamacol., 40:252-257 1988)).

Non-surfactants may include, for example, unsaturated cyclic ureas, 1-alkyl- and 1-alkenylazacyclo-alkanone derivatives (Lee et al., Critical Reviews in Therapeutic Drug Carrier Systems, page 92 (1991)); and non-steroidal anti-inflammatory agents such as diclofenac sodium, indomethacin and phenylbutazone (Yamashita et al., J. Pharm. Pharmacol., 39:621-626 1987)).

Prevention of degradation of siRNAs by microorganisms may be ensured by the inclusion of various antibacterial and antifungal agents including, for example, paraben, chlorobutanol, phenol, sorbic acid, etc.

One skilled in the art will appreciate that an effective amount of siRNA of the present invention may be determined empirically and may be employed in pure form or, where such forms exist, in a pharmaceutically acceptable salt, ester or prodrug form. A "therapeutically effective" amount of an embodiment of a siRNA-expressing vector composition may be determined by the amount needed to treat, manage, inhibit, prevent or ameliorate adverse conditions or symptoms of disease. Such determination may be made according to any method known in the art or described herein.

It will be understood that, when administering compositions of the present invention to a human patient, a "therapeutically effective" amount is expressed as total daily usage of the embodiment of the composition of the present invention and may be decided by the attending physician within the scope of sound medical judgment. The specific "therapeutically effective" dose level for a particular individual, subject, or patient may depend upon a variety of factors, including, for example, the type and degree of the cellular or physiological response desired, activity of the specific siRNA composition employed or expressed, the specific pharmaceutical formation or delivery method employed, the age, body weight, general health, sex and diet of the patient, the time of administration, route of administration, and rate of excretion of the composition, the specific dosage regimen, drugs used in combination or coincidental with the present composition, and other factors well known in the medical arts. For example, doses of embodiments of compositions of the present compositions may be started at levels lower than those expected to be necessary to achieve the desired therapeutic effect and to gradually increase the dosages until the desired effect is achieved.

One skilled in the art may also readily determine an appropriate dosage regimen for administering the embodiments of the compositions of the present invention to a given individual, subject, or patient. For example, a siRNA or vector composition may be administered to a subject once, such as by a single injection or deposition. Alternatively, a siRNA or vector composition may be administered to a subject multiple times daily or weekly. For example, compositions may be administered to a subject once weekly for a period of from about three to about twenty-eight weeks, such as from about seven to about ten weeks.

The present invention also includes methods involving co-administration of the compounds described herein with one or more additional active agents (e.g., immunosuppressive or chemotherapeutic agents). Indeed, it is a further aspect of this invention to provide methods for enhancing therapies and/or pharmaceutical compositions by co-administering a compound of embodiments of the present invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or other treatments may each be administered using different modes or different formulations.

EXAMPLES

The following examples are provided to demonstrate and further illustrate certain embodiments of the present invention and are not to be construed as limiting the scope thereof.

Example 1

Streptolysin-O (SLO; Sigma-Aldrich, St. Louis, Mo.) and reversible permeabilization were used for transfection. Cell lines and patient cells were evaluated for tolerance to SLO for transfection of siRNA using increasing concentrations of SLO, differing concentrations of cells and times of incubation, and Trypan blue staining, and the optimal effective method to enable successful gene silencing with no significant loss of cell number or viability was determined (Brito et al., J Immunol Methods. 2008; 333:147-155). Individual siRNA reagents for light and heavy chain genes and for scrambled control (si[-]) were produced to custom specifications by Dharmacon (Thermo Scientific, Lafayette, Colo.) and Integrated DNA Technologies (IDT, Coralville, Iowa). Assays were performed in 96-well plates with $1 \times 10^6$ cultured cells or 0.2 to $1 \times 10^6$ CD138-selected patient cells in a final volume of 50 ul containing optimal SLO, 250 nm siRNA per $10^6$ cells, and serum free medium. The selection and use of CD138+ patient cells is described (e.g., Comenzo et al., Amyloid. 2010; 17:61a; Zhou et al., Blood. 2008; 111:3403-3406; Zhou et al., Clin Lymphoma Myeloma Leuk. 2012; 12:49-58; Zhou et al., Blood. 2008; 111:549-557). After short-term incubation, cells were put in a larger volume of complete medium and incubated at 37° C. in 5% $CO_2$ incubator for 24 hours prior to being harvested for protein assessments.

One exemplary scheme for design of siRNA for plasma cells is depicted in FIG. 1, showing how the pool of 4 siRNA for lambda and kappa light chain constant regions (si[IgLC] and si[IgKC]) were developed and also how other pools of siRNA can be designed for the variable regions of the light and heavy chains of human plasma cells provided the sequences of the variable regions are known beforehand, permitting design of siRNA. Unlike the siRNA pools designed based on leader and variable region sequences, the si[IgLC] and si[IgKC] pools were designed based on consensus or shared coding sequences within lambda and kappa light chain constant region genes (Phipps et al. Exp Hematol; 38:1006-1013; Hovey et al., Gene Ther. 2011; 18:1150-1156; Ohno et al., J Immunol. 2002; 169:4039-4045). These are sequences that are highly specific to light chain constant region genes and avoid any overlap with members of the immunoglobulin superfamily of genes (Lefranc et al., Dev Comp Immunol. 2005; 29:185-203). siRNA compositions described herein (e.g., si[IgLC] and si[IgKC]), can be used off-the-shelf to stop immunoglobulin light chain expression with no a priori immunoglobulin gene sequencing required. The details of the target lambda constant region consensus sequences employed are shown in Table 1, the specific sequences of each of the 4 small interfering RNA in the si[IgLC] pool in Table 2, the details of the target kappa constant region consensus sequences employed in Table 3, and the specific sequences of each of the 4 small interfering RNA in the si[IgLC] pool in Table 4.

Figure 2:
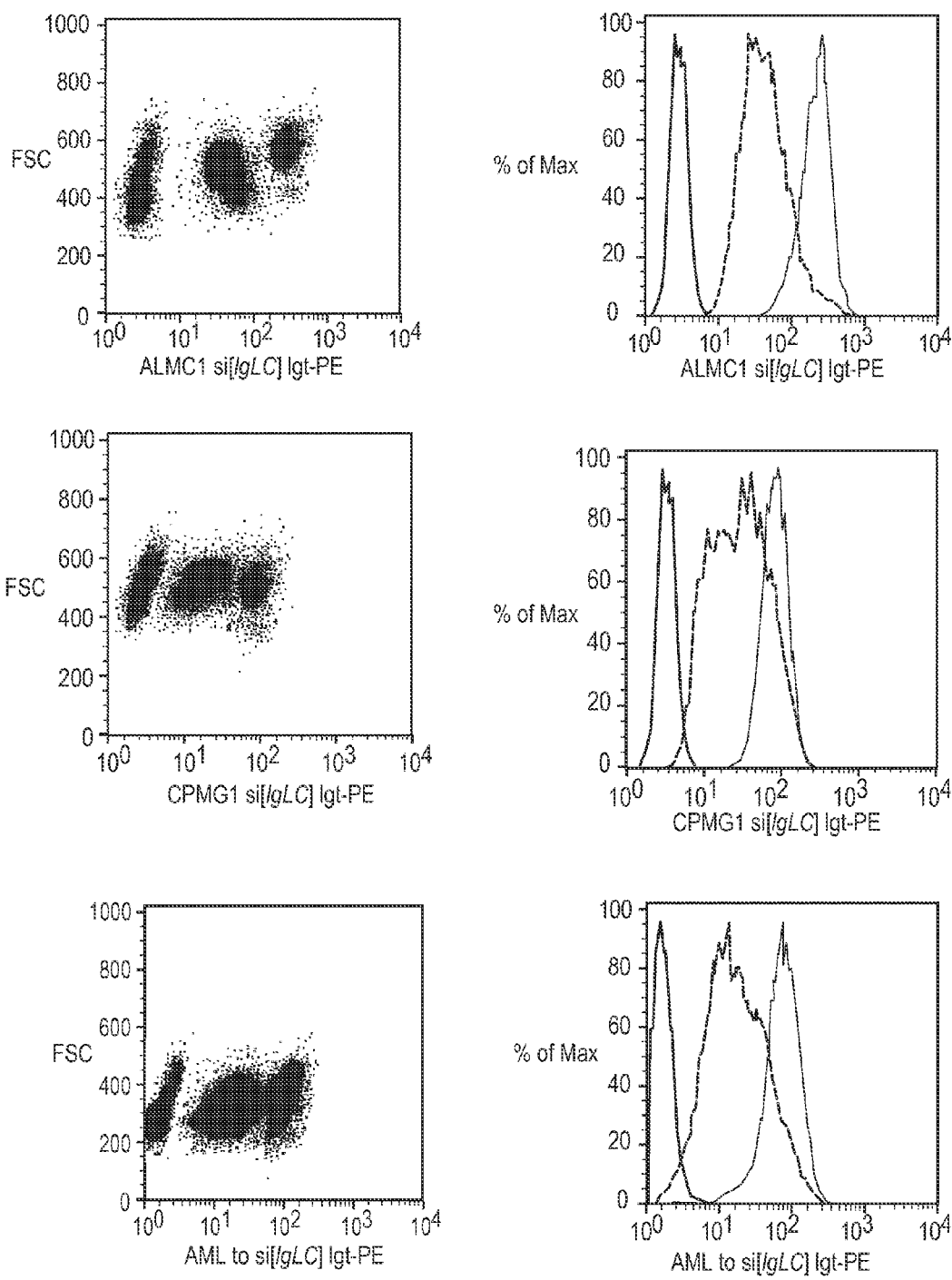
FIG. 2 shows si[IgLC] knockdown in human myeloma cell lines.
Figure 3:
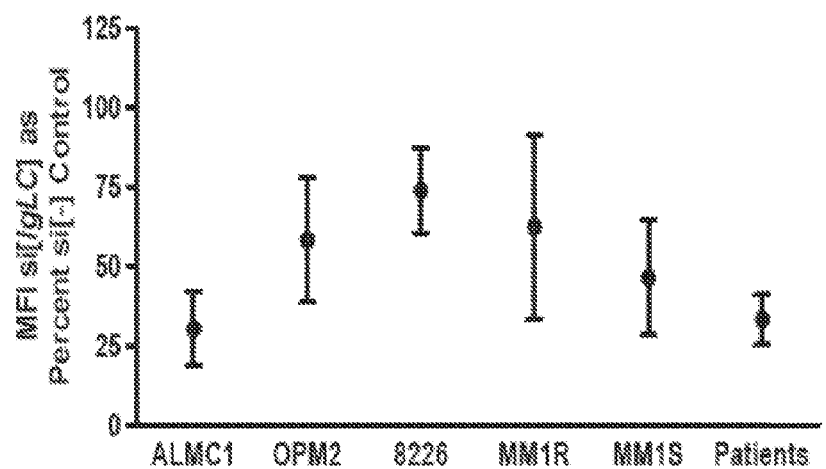
FIG. 3 shows the efficacy of si[IgLC] in reducing light chain protein expression by flow cytometry in lambda light chain producing myeloma cell lines and AL patient cells.
Figure 4:
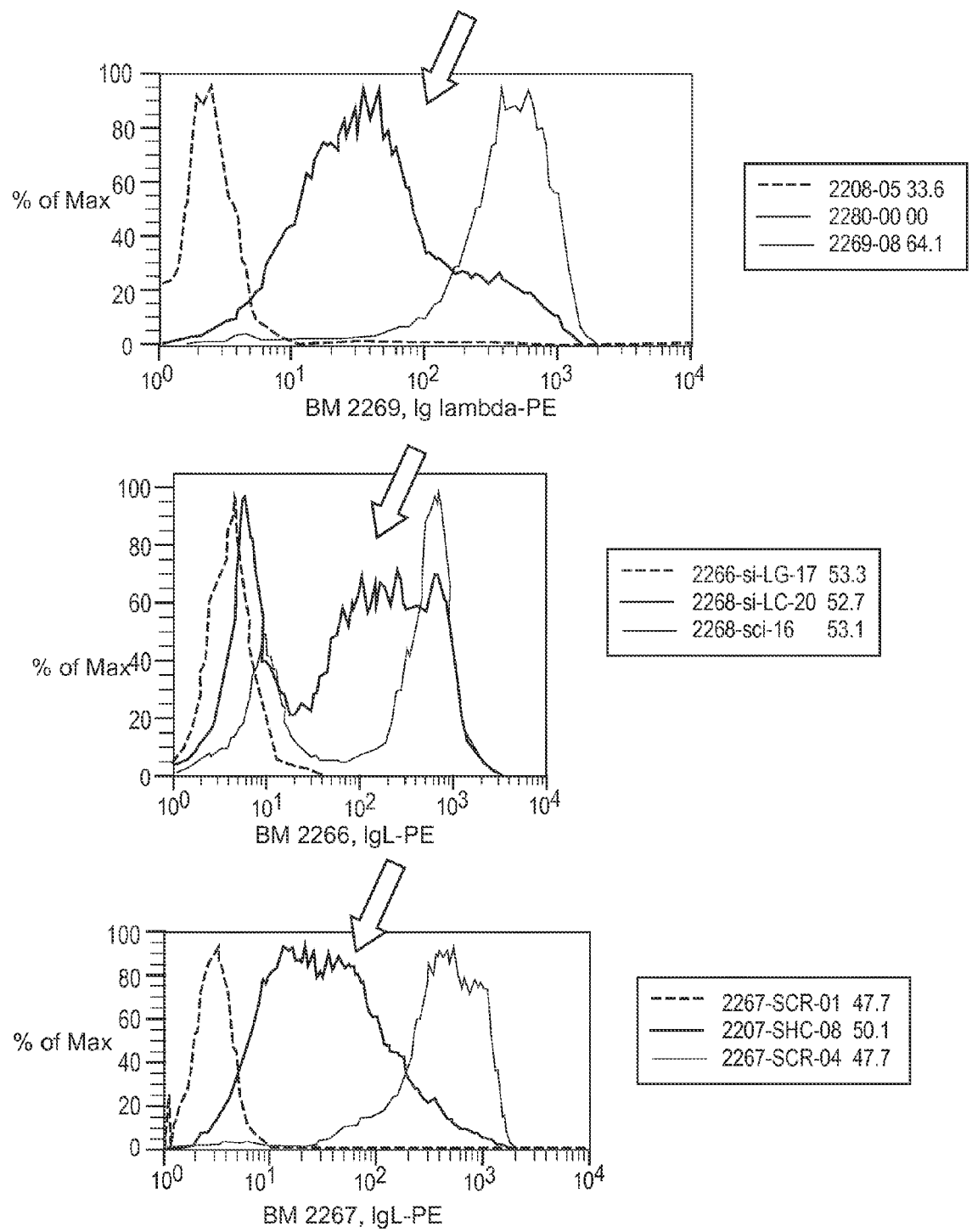
FIG. 4 shows patient samples showing reduced intracellular lambda light chains by flow cytometry at 24 hours after transfection with si[IgLC].
Figure 5:
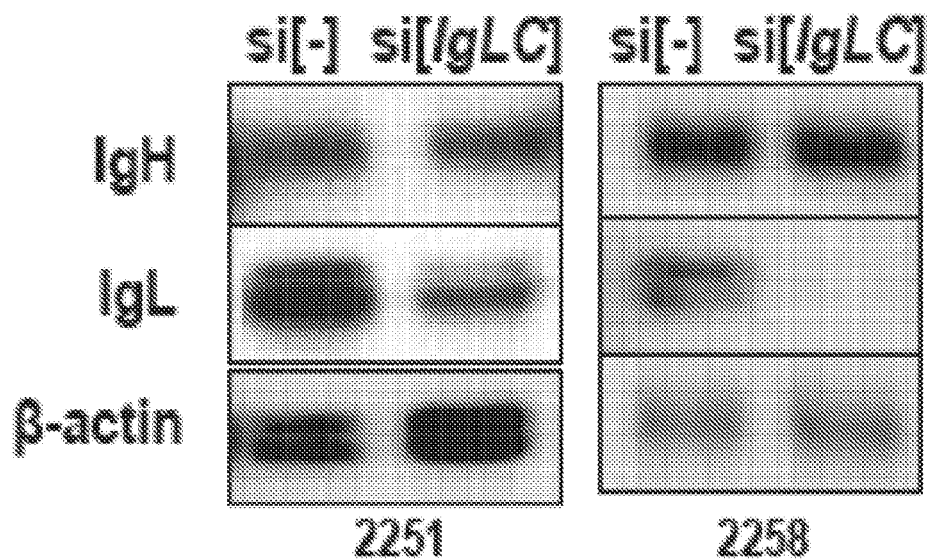
FIG. 5 shows immunoblot of lambda-restricted patient cells at 24 hours after treatment with si[IgLC] showing reduced lambda light chains.

The effectiveness of si[IgLC], the lambda light chain constant region siRNA pool inhibitor, in reducing light chain production in human myeloma cell lines is shown in FIG. 2. The individual flow cytometry plots are shown for ALMC1, OPM2 and MM cells demonstrating the reduced expression of light chains at 24 hours after treatment with si[IgLC] siRNA. FIG. 3 shows summary data of multiple experiments using si[IgLC] performed on different days in 5 human myeloma cell lines and in the cells of patients with monoclonal gammopathies making lambda light chains. The 5 cell lines are ALMC1, OPM2, RPMI 8226, MM1S and MM1R. All produce a lambda light chain monoclonal protein, and ALMC1 also produces a complete IgG lambda. The patient cells were collected on an IRB-approved protocol requiring written informed consent at the time of clinical marrow studies. Marrow aspirate cells were purified with CD138 immunoseparation on the day of the marrow procedure and used immediately in knockdown experiments. The patient samples were not subjected to light chain constant region gene sequencing studies; the si[IgLC] knockdowns were performed blindly with respect to gene sequence. In the cell lines lambda light chain protein expression was reduced by a median of 45%, and in the patient cells by 75%, at 24 hours. FIG. 4 shows flow cytometry plots from CD138-selected patient samples demonstrating a reduction in light chain expression in cells treated with si[IgLC]. FIG. 5 shows an immunoblot of patient cells after treatment with si[IgLC].

Figure 7:
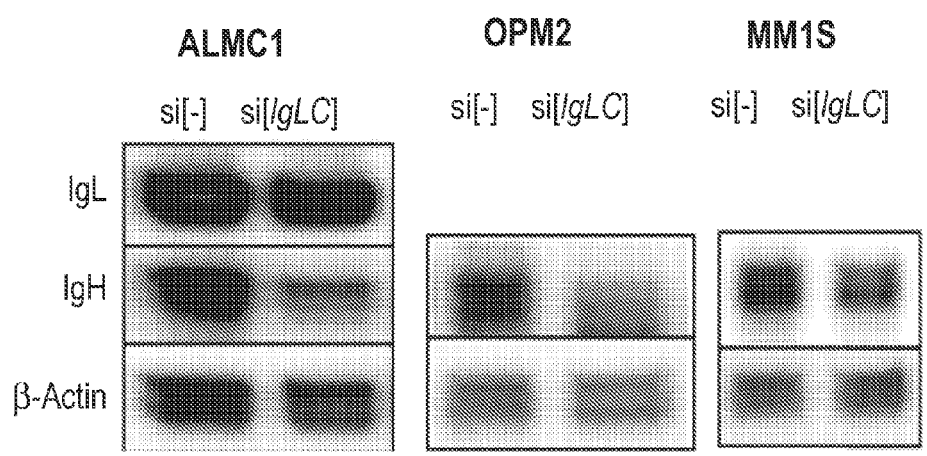
FIG. 7 shows light chain immunoblots of myeloma cell lines after si[IgLC].

FIG. 6 shows that knockdown of light and heavy chain expression in ALMC1 cells is feasible with specific variable region siRNA pools as indicated in FIG. 1. FIG. 6A shows reduced protein levels in ALMC1 cells at 24 hours after the specific knockdown of the light and the heavy chain genes; results of 11 experiments are summarized showing the aggregate reductions in intracellular mean fluorescent intensity by flow cytometry. FIG. 6B shows a plot of si[-] control and light chain knockdown cells demonstrating reduced intracellular staining for light chains, and in FIG. 6C shows immunoblots demonstrating reductions in light, heavy, or both light and heavy chains after specific siRNA treatments. The expression of light chains in ALMC1 cells can also be significantly reduced by si[IgLC] as shown in FIGS. 2 and 3, and reductions in light chains after treatment with si[IgLC] are also shown by immunoblots in ALMC1, OPM2, and MM as shown in FIG. 7. FIG. 8 shows the effective reduction of kappa light chain expression by immunoblot in si[IgKC] treated human myeloma cells. The human immunoglobulin light-chain constant region siRNA agents si[IgLC] and si[IgKC] can also be combined to knockdown both isotypes simultaneously as shown in FIG. 9.

Figure 11:
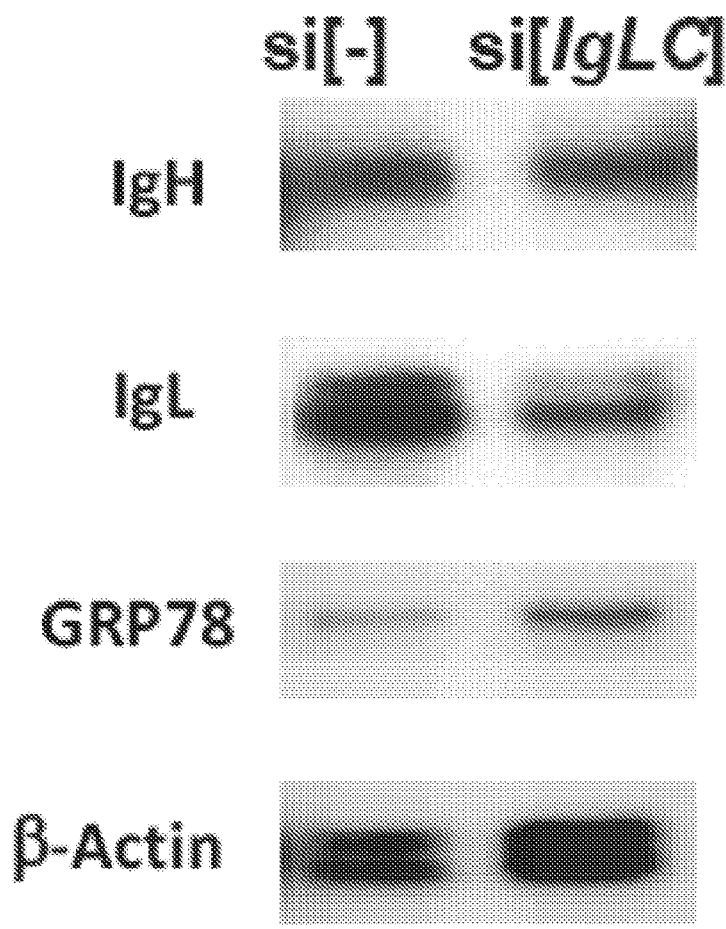
FIG. 11 shows immunoblots of a patient specimen showing reduction of lambda light chains and increase in GRP78 at 24 hours after si[IgLC] transfection.

Experiments conducted in ALMC1 human myeloma cells that make both an intact IgG lambda and free lambda light chains (Arendt et al., Blood. 2008; 112:1931-1941) demonstrated that the activation of the UPR in plasma cells making intact immunoglobulins containing light and heavy chains occurs after the knockdown of light chains and the creation of an excess of heavy chains. The excess unmated heavy chains become a sink for GRP78 as shown in FIG. 10. FIG. 10A shows the timeline of light chain (IgL) knockdown in ALMC1 cells and the persistence of heavy chains (IgH) over a 30 hour period, and FIG. 10B shows immunoblots (IB) of IgH, and in 10C of GRP78, immunoprecipitates (IP) at 16 and 30 hours after light chain knockdown. Pulldown of heavy chains contains GRP78 and pulldown of GRP78 contains heavy chains. These immunoprecipitates show a clear association between the unmated IgH and GRP78. FIG. 12A shows the timeline of UPR activation after light chain knockdown with evident increases in IRE-1α, GRP78 and CHOP at 16 hours, and FIG. 12B shows by real-time reverse transcription PCR the significant increases at 8 hours of message for the downstream UPR mediators GRP78, CHOP and XBP1s (Jager et al., Biol Cell. 2012; 104:259-270; Hetz et al., Mol Cell. 2009; 35:551-561). These results indicate that in plasma cells producing intact immunoglobulins, both light and heavy chains, knockdown of the light chain leaves unmated heavy chains within the cell that cause a marked increase in ER stress, are a sink for GRP78 and rapidly activate the UPR. FIG. 11 shows immunoblots from a specimen of patient cells that produce an intact IgGλ demonstrating increased levels of GRP78 associated with si[IgLC] treatment.

Activation of the UPR leads to apoptosis. FIG. 13A shows that caspase 3/7 activation, a marker of apoptosis, increases significantly with light chain knockdown in ALMC1 and ALMC2 cells but not with heavy chain or combined light and heavy chain knockdown. FIG. 13B shows that caspase3/7 activation increases over 24 hours after light chain knockdown, and FIG. 13C shows that caspase3/7 activation is quenched by a pan-caspase inhibitor. FIG. 13D shows a summary of results of 4 experiments using the JC-1 fluorescent dye that detects mitochondrial membrane depolarization, indicating that caspase-dependent mitochondrial depolarization occurs after light chain knockdown. The results in FIG. 14A are a typical AnnexinV/PI flow cytometry plot after lambda light chain knockdown (middle panel) and quenching of early and late apoptotic signal by a pan-caspase inhibitor (right panel). FIG. 14Bs shows the summary results for specific apoptosis due to lambda light chain knockdown using the calculation described in methods below. FIG. 15A shows, employing patient cells and si[IgLC], that si[IgLC] treatment of a patient's cells producing an intact IgGλ (tested in 4 wells), but not patient cells producing light chain (LC) only (n=3), causes increased levels of caspase 3/7 activation compared to control si[-] cells. FIG. 15B shows that si[IgLC] treatment of patients' cells producing an intact IgGλ (n=2), but not patients' cells producing light chain (LC) only (n=3), is associated with reduced numbers of viable cells by Trypan blue staining. In sum, these results clearly support the role of light chain knockdown as a trigger for the UPR and for cell death in plasma cells making an intact immunoglobulin due to the effects of excess unmated heavy chains. They provide support for the claim that si[IgLC] and si[IgKC] perform double duty in plasma cells, reducing light chain and intact immunoglobulin production and, in cells making intact immunoglobulins with light and heavy chains, causing cell death because of the toxicity of unmated heavy chains that cannot be secreted.

TABLE 1

The targeted gene sequences on the human IgLC immunoglobulin Lambda constant region are (as per ref|NT 011520.12| *Homo sapiens* chromosome 22 genomic contig, GRCh37.p5 Primary Assembly Length = 29755346):

1: (2633899)5'-CCAAACAAAGCAACAACAA-3'(2633917)   (SEQ ID NO: 1)

2: (2633946)5'-ACGCCUGAGCAGUGGAAGU-3'(2633964)   (SEQ ID NO: 2)

3: (2633778)5'-CUUCAAGCCAACAAGGCCA-3'(2633796)   (SEQ ID NO: 3)

4: (2633833)5'-CCGUGACAGUGGCCUGGAA-3'(2633851)   (SEQ ID NO: 4)

TABLE 2

The duplex sequences of the siRNA pool for the human Lambda light chain constant region (si[IgLC]) are:

1:
Sense: 5'-CCAAACAAAGCAACAACAA-3'          (SEQ ID NO: 5)
Anti-sense: 5'-UUGUUGUUGCUUUGUUUGG-3'     (SEQ ID NO: 6)

2:
Sense: 5'-ACGCCUGAGCAGUGGAAGU-3'          (SEQ ID NO: 7)
Anti-sense: 5'-ACUUCCACUGCUCAGGCGU-3'     (SEQ ID NO: 8)

3:
Sense: 5'-CUUCAAGCCAACAAGGCCA-3'          (SEQ ID NO: 9)
Anti-sense: 5'-UGGCCUUGUUGGCUUGAAG-3'     (SEQ ID NO: 10)

4:
Sense: 5'-CCGUGACAGUGGCCUGGAA-3'          (SEQ ID NO: 11)
Anti-sense: 5'-UUCCAGGCCACUGUCACGG-3'     (SEQ ID NO: 12)

TABLE 3

The targeted gene sequences on the human IgKC immunoglobulin Kapppa constant region are (as per ref|NT 022184.15| *Homo sapiens* chromosome 2 genomic contig, GRCh37.p5 Primary Assembly Length = 68452323):

1: (67978936)5'-GUAACUCCCAGGAGAGUGUCACAGA-3'(67978912)  (SEQ ID NO: 13)

2: (67978876)5'-GCACCCUGACGCUGAGCAAAGCAGA-3'(67978852)  (SEQ ID NO: 14)

3: (67979078)5'-GUGGCUGCACCAUCUGUCUUCAUCT-3'(67979054)  (SEQ ID NO: 15)

4: (67979026)5'-CUGGAACUGCCUCUGUUGUGUGCCT-3'(67979002)  (SEQ ID NO: 16)

TABLE 4

The duplex sequences of the siRNA pool for the human Kappa light chain constant region (si[IgKC]):

1:
Sense: 5'-GUAACUCCCAGGAGAGUGUCACAGA-3'            (SEQ ID NO: 17)
Anti-sense: 5'-UCUGUGACACUCUCCUGGGAGUUACCC-3'    (SEQ ID NO: 18)

2:
Sense: 5'-GCACCCUGACGCUGAGCAAAGCAGA-3'            (SEQ ID NO: 19)
Anti-sense: 5'-UCUGCUUUGCUCAGCGUCAGGGUGCUG-3'    (SEQ ID NO: 20)

TABLE 4-continued

The duplex sequences of the siRNA pool for the human Kappa light chain constant region (si[IgKC]):

3:
Sense: 5'-GUGGCUGCACCAUCUGUCUUCAUCT-3'          (SEQ ID NO: 21)
Anti-sense: 5'-AGAUGAAGACAGAUGGUGCAGCCACAG-3'(SEQ ID NO: 22)

4:
Sense: 5'-CUGGAACUGCCUCUGUUGUGUGCCT-3'          (SEQ ID NO: 23)
Anti-sense: 5'-AGGCACACAACAGAGGCAGUUCCAGAU-3'(SEQ ID NO: 24)

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a plurality of distinct nucleic acids that each hybridize to an immunoglobulin light chain constant region gene, wherein said nucleic acids comprise sequences selected from the group consisting of SEQ ID NOs: 5, 6, 7, 8, 9, 10, 11 and 12.

2. The composition of claim 1, wherein said nucleic acids are siRNAs having nucleic acid sequences selected from the group consisting of SEQ ID NOs: 5 and 6; 7 and 8; 9 and 10; and 11 and 12.

3. The composition of claim 1, wherein said composition comprises all of SEQ ID NOs: 5-12.

4. The composition of claim 1, wherein said nucleic acids consist of sequences selected from the group consisting of SEQ ID NOs: 5-12.

5. The composition of claim 1, wherein said composition is a pharmaceutical composition.

6. The composition of claim 5, wherein said composition further comprises a pharmaceutically acceptable carrier.

7. A kit comprising the composition of claim 1.

8. A composition comprising a plurality of distinct nucleic acids that each hybridize to an immunoglobulin light chain constant region gene, wherein said nucleic acids comprise a plurality of distinct nucleic acids comprising sequences selected from the group consisting of SEQ ID NOs: 17, 18, 19, 20, 21, 22, 23, and 24.

9. The composition of claim 8, wherein said nucleic acids are siRNAs having nucleic acid sequences selected from the group consisting of SEQ ID NOs: 17 and 18; 19 and 20; 21 and 22; and 23 and 24.

10. The composition of claim 8, wherein said composition comprises at least 4 distinct nucleic acids.

11. The composition of claim 8, wherein said composition comprises at least 6 distinct nucleic acids.

12. The composition of claim 8, wherein said composition comprises all of SEQ ID NOs: 17-24.

13. The composition of claim 1, wherein said composition is a pharmaceutical composition.

14. A kit comprising the composition of claim 8.

* * * * *

UNITED STATES PATENT AND TRADEMARK OFFICE
CERTIFICATE OF CORRECTION

Page 1 of 1

PATENT NO. : 9,593,332 B2
APPLICATION NO. : 14/760132
DATED : March 14, 2017
INVENTOR(S) : Raymond Comenzo et al.

It is certified that error appears in the above-identified patent and that said Letters Patent is hereby corrected as shown below:

In the Claims

Claim 13 reads:
"The composition of claim 1, wherein said composition is a pharmaceutical composition."

However, it should read:
"The composition of claim 8, wherein said composition is a pharmaceutical composition."

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*